United States Patent
Diolaiti et al.

(10) Patent No.: US 10,271,915 B2
(45) Date of Patent: Apr. 30, 2019

(54) APPLICATION OF FORCE FEEDBACK ON AN INPUT DEVICE TO URGE ITS OPERATOR TO COMMAND AN ARTICULATED INSTRUMENT TO A PREFERRED POSE

(71) Applicant: Intuitive Surgical Operations, Inc., Sunnyvale, CA (US)

(72) Inventors: Nicola Diolaiti, Menlo Park, CA (US); Paul E. Lilagan, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 115 days.

(21) Appl. No.: 15/296,488

(22) Filed: Oct. 18, 2016

(65) Prior Publication Data

US 2017/0035521 A1 Feb. 9, 2017

Related U.S. Application Data

(60) Division of application No. 13/292,760, filed on Nov. 9, 2011, now Pat. No. 9,492,927, which is a
(Continued)

(51) Int. Cl.
*A61B 34/00* (2016.01)
*A61B 90/30* (2016.01)
(Continued)

(52) U.S. Cl.
CPC ............ *A61B 34/76* (2016.02); *A61B 34/10* (2016.02); *A61B 34/30* (2016.02); *A61B 34/35* (2016.02);
(Continued)

(58) Field of Classification Search
CPC ......... A61B 34/76; A61B 90/30; A61B 34/10; A61B 34/37; A61B 34/35; A61B 34/77;
(Continued)

(56) References Cited

U.S. PATENT DOCUMENTS 3,628,535 A 12/1971 Ostrowsky et al.
3,818,284 A 6/1974 Deversterre et al.
(Continued)

FOREIGN PATENT DOCUMENTS

CN 101160104 A 4/2008
EP 514584 A2 11/1992
(Continued)

OTHER PUBLICATIONS

3D Slicer web site,http//www.slicer.org,2003.
(Continued)

*Primary Examiner* — Abby Y Lin

(57) ABSTRACT

A medical robotic system includes an entry guide with articulated instruments extending out of its distal end. A controller is configured to command manipulation an articulated instrument in response to operator manipulation of an associated input device while generating a force command to the input device that nudges the operator to command the instrument to a preferred pose. When a transition is to occur between first and second preferred poses, one is phased in while the other is phased out. Virtual barriers may be imposed to prevent the articulated instrument from being commanded to an undesirable pose.

20 Claims, 22 Drawing Sheets

Related U.S. Application Data continuation-in-part of application No. 12/704,669, filed on Feb. 12, 2010, now Pat. No. 8,918,211, and a continuation-in-part of application No. 12/613,328, filed on Nov. 5, 2009, now Pat. No. 9,084,623, which is a continuation-in-part of application No. 12/541,913, filed on Aug. 15, 2009, now Pat. No. 8,903,546.

(51) Int. Cl.

| | | |
|---|---|---|
| A61B 34/30 | (2016.01) | |
| A61B 34/10 | (2016.01) | |
| A61B 34/37 | (2016.01) | |
| B25J 13/02 | (2006.01) | |
| B25J 9/16 | (2006.01) | |
| A61B 34/35 | (2016.01) | |
| A61B 90/00 | (2016.01) | |

(52) U.S. Cl.
CPC .............. *A61B 34/37* (2016.02); *A61B 34/77* (2016.02); *A61B 90/30* (2016.02); *B25J 9/1689* (2013.01); *B25J 13/025* (2013.01); *A61B 34/25* (2016.02); *A61B 90/361* (2016.02); *A61B 2034/102* (2016.02); *A61B 2034/305* (2016.02); *A61B 2090/306* (2016.02); *F04C 2270/041* (2013.01); *G05B 2219/45117* (2013.01)

(58) Field of Classification Search
CPC ... A61B 34/30; A61B 2090/306; A61B 34/25; A61B 90/361; A61B 2034/305; A61B 2034/102; B25J 9/1689; B25J 9/065; B25J 9/1625; B25J 13/025; F04C 2270/041; G05B 2219/45117

See application file for complete search history.

(56) References Cited

U.S. PATENT DOCUMENTS

| | | |
|---|---|---|
| 3,905,215 A | 9/1975 | Wright |
| 3,923,166 A | 12/1975 | Fletcher et al. |
| 4,150,326 A | 4/1979 | Engelberger et al. |
| 4,349,837 A | 9/1982 | Hinds |
| 4,577,621 A | 3/1986 | Patel |
| 4,588,348 A | 5/1986 | Beni et al. |
| 4,644,237 A | 2/1987 | Frushour et al. |
| 4,672,963 A | 6/1987 | Barken |
| 4,722,056 A | 1/1988 | Roberts et al. |
| 4,759,074 A | 7/1988 | Iadipaolo et al. |
| 4,762,455 A | 8/1988 | Coughlan et al. |
| 4,762,456 A | 8/1988 | Nelson |
| 4,791,934 A | 12/1988 | Brunnett |
| 4,815,450 A | 3/1989 | Patel |
| 4,831,549 A | 5/1989 | Red et al. |
| 4,833,383 A | 5/1989 | Skarr et al. |
| 4,837,703 A | 6/1989 | Kakazu et al. |
| 4,837,734 A | 6/1989 | Ichikawa et al. |
| 4,839,838 A | 6/1989 | Labiche et al. |
| 4,853,874 A | 8/1989 | Iwamoto et al. |
| 4,858,149 A | 8/1989 | Quarendon |
| 4,860,215 A | 8/1989 | Seraji |
| 4,863,133 A | 9/1989 | Bonnell |
| 4,891,767 A | 1/1990 | Rzasa et al. |
| 4,942,539 A | 7/1990 | McGee et al. |
| 4,979,949 A | 12/1990 | Matsen, III |
| 4,984,157 A | 1/1991 | Cline et al. |
| 4,989,253 A | 1/1991 | Liang et al. |
| 5,046,022 A | 9/1991 | Conway et al. |
| 5,053,976 A | 10/1991 | Nose et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,174,276 A | 12/1992 | Crockard |
| 5,176,702 A | 1/1993 | Bales et al. |
| 5,182,641 A | 1/1993 | Diner et al. |
| 5,184,009 A | 2/1993 | Wright et al. |
| 5,184,601 A | 2/1993 | Putman |
| 5,187,796 A | 2/1993 | Wang et al. |
| 5,217,003 A | 6/1993 | Wilk |
| 5,230,338 A | 7/1993 | Allen et al. |
| 5,230,623 A | 7/1993 | Guthrie et al. |
| 5,235,510 A | 8/1993 | Yamada et al. |
| 5,239,246 A | 8/1993 | Kim |
| 5,251,127 A | 10/1993 | Raab |
| 5,251,611 A | 10/1993 | Zehel et al. |
| 5,257,203 A | 10/1993 | Riley et al. |
| 5,261,404 A | 11/1993 | Mick et al. |
| 5,266,875 A | 11/1993 | Slotine et al. |
| 5,279,309 A | 1/1994 | Taylor et al. |
| 5,299,288 A | 3/1994 | Glassman et al. |
| 5,313,306 A | 5/1994 | Kuban et al. |
| 5,321,353 A | 6/1994 | Furness |
| 5,337,733 A | 8/1994 | Bauerfeind et al. |
| 5,341,950 A | 8/1994 | Sinz |
| 5,343,385 A | 8/1994 | Joskowicz et al. |
| 5,368,015 A | 11/1994 | Wilk |
| 5,368,428 A | 11/1994 | Hussey et al. |
| 5,382,885 A | 1/1995 | Salcudean et al. |
| 5,397,323 A | 3/1995 | Taylor et al. |
| 5,402,801 A | 4/1995 | Taylor |
| 5,408,409 A | 4/1995 | Glassman et al. |
| 5,417,210 A | 5/1995 | Funda et al. |
| 5,430,643 A | 7/1995 | Seraji |
| 5,445,166 A | 8/1995 | Taylor |
| 5,454,827 A | 10/1995 | Aust et al. |
| 5,474,571 A | 12/1995 | Lang |
| 5,482,029 A | 1/1996 | Sekiguchi et al. |
| 5,493,595 A | 2/1996 | Schoolman |
| 5,503,320 A | 4/1996 | Webster et al. |
| 5,515,478 A | 5/1996 | Wang |
| 5,524,180 A | 6/1996 | Wang et al. |
| 5,528,955 A | 6/1996 | Hannaford et al. |
| 5,531,742 A | 7/1996 | Barken |
| 5,551,432 A | 9/1996 | Iezzi |
| 5,553,198 A | 9/1996 | Wang et al. |
| 5,572,999 A | 11/1996 | Funda et al. |
| 5,601,549 A | 2/1997 | Miyagi |
| 5,617,858 A | 4/1997 | Taverna et al. |
| 5,624,398 A | 4/1997 | Smith et al. |
| 5,631,973 A | 5/1997 | Green |
| 5,638,819 A | 6/1997 | Manwaring et al. |
| 5,657,429 A | 8/1997 | Wang et al. |
| 5,695,500 A | 12/1997 | Taylor et al. |
| 5,704,897 A | 1/1998 | Truppe |
| 5,715,729 A | 2/1998 | Toyama et al. |
| 5,737,500 A | 4/1998 | Seraji et al. |
| 5,748,767 A | 5/1998 | Raab |
| 5,749,362 A | 5/1998 | Funda et al. |
| 5,754,741 A | 5/1998 | Wang et al. |
| 5,755,725 A | 5/1998 | Druais |
| 5,759,151 A | 6/1998 | Sturges |
| 5,759,153 A | 6/1998 | Webler et al. |
| 5,762,458 A | 6/1998 | Wang et al. |
| 5,765,561 A | 6/1998 | Chen et al. |
| 5,784,542 A | 7/1998 | Ohm et al. |
| 5,788,688 A | 8/1998 | Bauer et al. |
| 5,791,231 A | 8/1998 | Cohn et al. |
| 5,792,135 A | 8/1998 | Madhani et al. |
| 5,797,849 A | 8/1998 | Vesely et al. |
| 5,797,900 A | 8/1998 | Madhani et al. |
| 5,807,377 A | 9/1998 | Madhani et al. |
| 5,808,665 A | 9/1998 | Green |
| 5,810,008 A | 9/1998 | Dekel et al. |
| 5,810,880 A | 9/1998 | Jensen et al. |
| 5,814,038 A | 9/1998 | Jensen et al. |
| 5,815,640 A | 9/1998 | Wang et al. |
| 5,817,022 A | 10/1998 | Vesely |
| 5,820,545 A | 10/1998 | Arbter et al. |
| 5,820,623 A | 10/1998 | Ng |

(56) References Cited

U.S. PATENT DOCUMENTS

| | | |
|---|---|---|
| 5,831,408 A | 11/1998 | Jacobus et al. |
| 5,835,693 A | 11/1998 | Lynch et al. |
| 5,836,880 A | 11/1998 | Pratt |
| 5,841,950 A | 11/1998 | Wang et al. |
| 5,842,473 A | 12/1998 | Fenster et al. |
| 5,842,993 A | 12/1998 | Eichelberger et al. |
| 5,853,367 A | 12/1998 | Chalek et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,877,819 A | 3/1999 | Branson |
| 5,878,193 A | 3/1999 | Wang et al. |
| 5,887,121 A | 3/1999 | Funda et al. |
| 5,907,664 A | 5/1999 | Wang et al. |
| 5,911,036 A | 6/1999 | Wright et al. |
| 5,931,832 A | 8/1999 | Jensen |
| 5,938,678 A | 8/1999 | Zirps et al. |
| 5,950,629 A | 9/1999 | Taylor et al. |
| 5,964,707 A | 10/1999 | Fenster et al. |
| 5,971,976 A | 10/1999 | Wang et al. |
| 5,980,460 A | 11/1999 | Oestensen et al. |
| 5,980,461 A | 11/1999 | Rajan |
| 5,987,591 A | 11/1999 | Jyumonji |
| 5,993,390 A | 11/1999 | Savord et al. |
| 5,993,391 A | 11/1999 | Kamiyama |
| 6,019,724 A | 2/2000 | Gronningsaeter et al. |
| 6,036,637 A | 3/2000 | Kudo |
| 6,059,718 A | 5/2000 | Taniguchi et al. |
| 6,063,095 A | 5/2000 | Wang et al. |
| 6,072,466 A | 6/2000 | Shah et al. |
| 6,083,170 A | 7/2000 | Ben-Haim |
| 6,084,371 A | 7/2000 | Kress et al. |
| 6,096,025 A | 8/2000 | Borders |
| 6,115,053 A | 9/2000 | Perlin |
| 6,120,433 A | 9/2000 | Mizuno et al. |
| 6,129,670 A | 10/2000 | Burdette et al. |
| 6,184,868 B1 | 2/2001 | Shahoian et al. |
| 6,196,081 B1 | 3/2001 | Yau |
| 6,201,984 B1 | 3/2001 | Funda et al. |
| 6,204,620 B1 | 3/2001 | McGee et al. |
| 6,224,542 B1 | 5/2001 | Chang et al. |
| 6,226,566 B1 | 5/2001 | Funda et al. |
| 6,241,725 B1 | 6/2001 | Cosman |
| 6,243,624 B1 | 6/2001 | Wu et al. |
| 6,246,200 B1 | 6/2001 | Blumenkranz et al. |
| 6,256,529 B1 | 7/2001 | Holupka et al. |
| 6,270,453 B1 | 8/2001 | Sakai |
| 6,292,712 B1 | 9/2001 | Bullen |
| 6,307,285 B1 | 10/2001 | Delson et al. |
| 6,312,435 B1 | 11/2001 | Wallace et al. |
| 6,325,808 B1 | 12/2001 | Bernard et al. |
| 6,330,837 B1 | 12/2001 | Charles et al. |
| 6,331,181 B1 | 12/2001 | Tierney et al. |
| 6,342,889 B1 | 1/2002 | Callahan |
| 6,358,749 B1 | 3/2002 | Orthman |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,402,737 B1 | 6/2002 | Tajima et al. |
| 6,424,885 B1 | 7/2002 | Niemeyer et al. |
| 6,425,865 B1 | 7/2002 | Salcudean et al. |
| 6,434,416 B1 | 8/2002 | Mizoguchi et al. |
| 6,436,107 B1 | 8/2002 | Wang et al. |
| 6,442,417 B1 | 8/2002 | Shahidi et al. |
| 6,456,901 B1 | 9/2002 | Xi et al. |
| 6,459,926 B1 | 10/2002 | Nowlin et al. |
| 6,468,265 B1 | 10/2002 | Evans et al. |
| 6,493,608 B1 | 12/2002 | Niemeyer |
| 6,522,906 B1 | 2/2003 | Salisbury, Jr. et al. |
| 6,522,908 B1 | 2/2003 | Miyashita et al. |
| 6,547,782 B1 | 4/2003 | Taylor |
| 6,550,757 B2 | 4/2003 | Sesek |
| 6,569,084 B1 | 5/2003 | Mizuno et al. |
| 6,574,355 B2 | 6/2003 | Green |
| 6,594,522 B1 | 7/2003 | Korenaga |
| 6,594,552 B1 | 7/2003 | Nowlin et al. |
| 6,599,247 B1 | 7/2003 | Stetten |
| 6,602,185 B1 | 8/2003 | Uchikubo |
| 6,620,173 B2 | 9/2003 | Gerbi et al. |
| 6,642,836 B1 | 11/2003 | Wang et al. |
| 6,643,563 B2 | 11/2003 | Hosek et al. |
| 6,645,196 B1 | 11/2003 | Nixon et al. |
| 6,648,816 B2 | 11/2003 | Irion et al. |
| 6,654,031 B1 | 11/2003 | Ito et al. |
| 6,659,939 B2 | 12/2003 | Moll et al. |
| 6,665,554 B1 | 12/2003 | Charles et al. |
| 6,671,581 B2 | 12/2003 | Niemeyer et al. |
| 6,676,669 B2 | 1/2004 | Charles et al. |
| 6,699,177 B1 | 3/2004 | Wang et al. |
| 6,702,736 B2 | 3/2004 | Chen et al. |
| 6,714,839 B2 | 3/2004 | Salisbury et al. |
| 6,765,569 B2 | 7/2004 | Neumann et al. |
| 6,770,081 B1 | 8/2004 | Cooper et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,827,712 B2 | 12/2004 | Tovey et al. |
| 6,837,883 B2 | 1/2005 | Moll et al. |
| 6,847,922 B1 | 1/2005 | Wampler, II |
| 6,852,107 B2 | 2/2005 | Wang et al. |
| 6,876,891 B1 | 4/2005 | Schuler et al. |
| 6,905,460 B2 | 6/2005 | Wang et al. |
| 6,926,709 B2 | 8/2005 | Bieger et al. |
| 6,960,162 B2 | 11/2005 | Saadat et al. |
| 6,984,203 B2 | 1/2006 | Tartaglia et al. |
| 6,991,627 B2 | 1/2006 | Madhani et al. |
| 7,041,053 B2 | 5/2006 | Miyake |
| 7,107,090 B2 | 9/2006 | Salisbury et al. |
| 7,107,124 B2 | 9/2006 | Green |
| 7,144,367 B2 | 12/2006 | Chen et al. |
| 7,155,315 B2 | 12/2006 | Niemeyer et al. |
| 7,155,316 B2 | 12/2006 | Sutherland et al. |
| 7,181,315 B2 | 2/2007 | Watanabe et al. |
| 7,194,118 B1 | 3/2007 | Harris et al. |
| 7,302,288 B1 | 11/2007 | Schellenberg |
| 7,413,565 B2 | 8/2008 | Wang et al. |
| 7,491,198 B2 | 2/2009 | Kockro |
| 7,493,153 B2 | 2/2009 | Ahmed et al. |
| 7,574,250 B2 | 8/2009 | Niemeyer |
| 7,725,214 B2 | 5/2010 | Diolaiti |
| 7,806,891 B2 | 10/2010 | Nowlin et al. |
| 7,819,859 B2 | 10/2010 | Prisco et al. |
| 7,963,913 B2 | 6/2011 | Devengenzo et al. |
| 7,979,157 B2 | 7/2011 | Anvari |
| 7,996,110 B2 | 8/2011 | Lipow et al. |
| 7,998,058 B2 | 8/2011 | Kura et al. |
| 8,004,229 B2 | 8/2011 | Nowlin et al. |
| 8,005,571 B2 | 8/2011 | Sutherland et al. |
| 8,062,288 B2 | 11/2011 | Cooper et al. |
| 8,108,072 B2 | 1/2012 | Zhao et al. |
| 8,120,301 B2 | 2/2012 | Goldberg et al. |
| 8,130,907 B2 | 3/2012 | Maurer, Jr. et al. |
| 8,155,479 B2 | 4/2012 | Hoffman et al. |
| 8,170,716 B2 | 5/2012 | Coste-Maniere et al. |
| 8,175,861 B2 | 5/2012 | Huang et al. |
| 8,221,304 B2 | 7/2012 | Shioda et al. |
| 8,256,319 B2 | 9/2012 | Cooper et al. |
| 8,306,656 B1 | 11/2012 | Schaible et al. |
| 8,315,720 B2 | 11/2012 | Mohr et al. |
| 8,335,590 B2 | 12/2012 | Costa et al. |
| 8,398,541 B2 | 3/2013 | Dimaio et al. |
| 8,541,970 B2 | 9/2013 | Nowlin et al. |
| 8,554,368 B2 | 10/2013 | Fielding et al. |
| 8,620,473 B2 | 12/2013 | Diolaiti et al. |
| 8,624,537 B2 | 1/2014 | Nowlin et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,864,652 B2 | 10/2014 | Diolaiti et al. |
| 8,903,546 B2 | 12/2014 | Diolaiti et al. |

(56) References Cited

U.S. PATENT DOCUMENTS

| | | |
|---|---|---|
| 8,918,211 B2 | 12/2014 | Diolaiti et al. |
| 8,944,070 B2 | 2/2015 | Guthart et al. |
| 9,084,623 B2 | 7/2015 | Gomez et al. |
| 9,089,256 B2 | 7/2015 | Tognaccini et al. |
| 9,101,397 B2 | 8/2015 | Guthart et al. |
| 9,138,129 B2 | 9/2015 | Diolaiti |
| 9,232,984 B2 | 1/2016 | Guthart et al. |
| 9,333,042 B2 | 5/2016 | Diolaiti et al. |
| 9,345,387 B2 | 5/2016 | Larkin |
| 9,469,034 B2 | 10/2016 | Diolaiti et al. |
| 9,492,927 B2 | 11/2016 | Diolaiti et al. |
| 9,516,996 B2 | 12/2016 | Diolaiti et al. |
| 9,565,990 B2 | 2/2017 | Lee et al. |
| 9,622,826 B2 | 4/2017 | Diolaiti et al. |
| 9,717,563 B2 | 8/2017 | Tognaccini et al. |
| 9,718,190 B2 | 8/2017 | Larkin et al. |
| 9,949,798 B2 | 4/2018 | Weir et al. |
| 2001/0035871 A1 | 11/2001 | Bieger et al. |
| 2002/0044104 A1 | 4/2002 | Friedrich et al. |
| 2002/0045888 A1 | 4/2002 | Ramans et al. |
| 2002/0089544 A1 | 7/2002 | Jahn et al. |
| 2002/0120188 A1 | 8/2002 | Brock et al. |
| 2002/0156345 A1 | 10/2002 | Eppler et al. |
| 2002/0193800 A1 | 12/2002 | Kienzle, III |
| 2003/0023347 A1 | 1/2003 | Konno et al. |
| 2003/0032878 A1 | 2/2003 | Shahidi |
| 2003/0055410 A1 | 3/2003 | Evans et al. |
| 2003/0060927 A1 | 3/2003 | Gerbi et al. |
| 2003/0109780 A1 | 6/2003 | Coste-Maniere et al. |
| 2003/0114730 A1 | 6/2003 | Hale et al. |
| 2003/0144649 A1 | 7/2003 | Ghodoussi et al. |
| 2003/0167103 A1 | 9/2003 | Tang et al. |
| 2003/0225479 A1 | 12/2003 | Waled |
| 2004/0024311 A1 | 2/2004 | Quaid et al. |
| 2004/0034283 A1 | 2/2004 | Quaid, III |
| 2004/0039485 A1 | 2/2004 | Niemeyer et al. |
| 2004/0044295 A1 | 3/2004 | Reinert et al. |
| 2004/0046711 A1 | 3/2004 | Triebfuerst |
| 2004/0046916 A1 | 3/2004 | Lyu et al. |
| 2004/0049205 A1 | 3/2004 | Lee et al. |
| 2004/0077940 A1 | 4/2004 | Kienzle et al. |
| 2004/0106916 A1 | 6/2004 | Quaid et al. |
| 2004/0176751 A1 | 9/2004 | Weitzner et al. |
| 2004/0189675 A1 | 9/2004 | Pretlove et al. |
| 2004/0225183 A1 | 11/2004 | Michlitsch et al. |
| 2004/0238732 A1 | 12/2004 | State et al. |
| 2004/0243147 A1 | 12/2004 | Lipow |
| 2004/0249508 A1 | 12/2004 | Suita et al. |
| 2004/0254454 A1 | 12/2004 | Kockro |
| 2004/0254679 A1 | 12/2004 | Nagasaka |
| 2005/0022158 A1 | 1/2005 | Launay et al. |
| 2005/0054895 A1 | 3/2005 | Hoeg et al. |
| 2005/0059960 A1 | 3/2005 | Simaan et al. |
| 2005/0096502 A1 | 5/2005 | Khalili |
| 2005/0096892 A1 | 5/2005 | Watanabe et al. |
| 2005/0107680 A1 | 5/2005 | Kopf et al. |
| 2005/0113640 A1 | 5/2005 | Saadat et al. |
| 2005/0166413 A1 | 8/2005 | Crampton et al. |
| 2005/0203380 A1 | 9/2005 | Sauer et al. |
| 2005/0228365 A1 | 10/2005 | Wang et al. |
| 2005/0251113 A1 | 11/2005 | Kienzle, III |
| 2005/0267359 A1 | 12/2005 | Hussaini et al. |
| 2006/0058988 A1 | 3/2006 | Defranoux et al. |
| 2006/0142657 A1 | 6/2006 | Quaid et al. |
| 2006/0149129 A1 | 7/2006 | Watts et al. |
| 2006/0161045 A1 | 7/2006 | Merril et al. |
| 2006/0161138 A1 | 7/2006 | Orban, III |
| 2006/0178559 A1 | 8/2006 | Kumar et al. |
| 2006/0258938 A1 | 11/2006 | Hoffman et al. |
| 2006/0261770 A1 | 11/2006 | Kishi et al. |
| 2007/0013336 A1 | 1/2007 | Nowlin et al. |
| 2007/0016174 A1 | 1/2007 | Millman et al. |
| 2007/0021738 A1 | 1/2007 | Hasser et al. |
| 2007/0038080 A1 | 2/2007 | Salisbury, Jr. et al. |
| 2007/0060879 A1 | 3/2007 | Weitzner et al. |
| 2007/0071310 A1 | 3/2007 | Kobayashi et al. |
| 2007/0081714 A1 | 4/2007 | Wallack et al. |
| 2007/0106307 A1 | 5/2007 | Bodduluri et al. |
| 2007/0135803 A1 | 6/2007 | Belson |
| 2007/0138992 A1 | 6/2007 | Prisco et al. |
| 2007/0142825 A1 | 6/2007 | Prisco et al. |
| 2007/0142968 A1 | 6/2007 | Prisco et al. |
| 2007/0144298 A1 | 6/2007 | Miller |
| 2007/0156285 A1 | 7/2007 | Sillman et al. |
| 2007/0177009 A1 | 8/2007 | Bayer et al. |
| 2007/0197896 A1 | 8/2007 | Moll et al. |
| 2007/0229015 A1 | 10/2007 | Yoshida et al. |
| 2007/0255454 A1 | 11/2007 | Dariush |
| 2007/0265491 A1 | 11/2007 | Krag et al. |
| 2007/0270650 A1 | 11/2007 | Eno et al. |
| 2007/0270685 A1 | 11/2007 | Kang et al. |
| 2007/0283970 A1 | 12/2007 | Mohr et al. |
| 2007/0287884 A1 | 12/2007 | Schena |
| 2007/0287992 A1 | 12/2007 | Diolaiti et al. |
| 2007/0296366 A1 | 12/2007 | Quaid et al. |
| 2008/0004603 A1 | 1/2008 | Larkin et al. |
| 2008/0033240 A1 | 2/2008 | Hoffman et al. |
| 2008/0065099 A1 | 3/2008 | Cooper et al. |
| 2008/0065105 A1 | 3/2008 | Larkin et al. |
| 2008/0071291 A1 | 3/2008 | Duval et al. |
| 2008/0081992 A1 | 4/2008 | Kagermeier |
| 2008/0118115 A1 | 5/2008 | Williamson |
| 2008/0140087 A1 | 6/2008 | Barbagli |
| 2008/0161830 A1 | 7/2008 | Sutherland et al. |
| 2008/0188986 A1 | 8/2008 | Hoppe |
| 2008/0243142 A1 | 10/2008 | Gildenberg |
| 2008/0247506 A1 | 10/2008 | Maschke |
| 2008/0287963 A1 | 11/2008 | Rogers et al. |
| 2009/0005640 A1 | 1/2009 | Fehre et al. |
| 2009/0012531 A1 | 1/2009 | Quaid et al. |
| 2009/0024142 A1 | 1/2009 | Ruiz Morales |
| 2009/0088634 A1 | 4/2009 | Zhao et al. |
| 2009/0105750 A1 | 4/2009 | Price et al. |
| 2009/0192523 A1 | 7/2009 | Larkin et al. |
| 2009/0192524 A1 | 7/2009 | Itkowitz et al. |
| 2009/0228145 A1 | 9/2009 | Hodgson et al. |
| 2009/0248036 A1 | 10/2009 | Hoffman et al. |
| 2009/0259105 A1 | 10/2009 | Miyano et al. |
| 2009/0326322 A1 | 12/2009 | Diolaiti |
| 2009/0326552 A1 | 12/2009 | Diolaiti |
| 2009/0326553 A1 | 12/2009 | Mustufa et al. |
| 2009/0326711 A1 | 12/2009 | Chang et al. |
| 2010/0004505 A1 | 1/2010 | Umemoto et al. |
| 2010/0036198 A1 | 2/2010 | Tacchino et al. |
| 2010/0106356 A1 | 4/2010 | Trepagnier et al. |
| 2010/0169815 A1 | 7/2010 | Zhao et al. |
| 2010/0198232 A1 | 8/2010 | Diolaiti |
| 2010/0228264 A1 | 9/2010 | Robinson et al. |
| 2010/0249657 A1 | 9/2010 | Nycz et al. |
| 2010/0317965 A1 | 12/2010 | Itkowitz et al. |
| 2010/0331855 A1 | 12/2010 | Zhao et al. |
| 2010/0331856 A1 | 12/2010 | Carlson et al. |
| 2011/0071675 A1 | 3/2011 | Wells et al. |
| 2011/0196199 A1 | 8/2011 | Donhowe et al. |
| 2011/0290856 A1 | 12/2011 | Shelton, IV et al. |
| 2011/0313573 A1 | 12/2011 | Schreiber et al. |
| 2012/0059391 A1 | 3/2012 | Diolaiti et al. |
| 2012/0132450 A1 | 5/2012 | Timm et al. |
| 2012/0154564 A1 | 6/2012 | Hoffman et al. |
| 2013/0178868 A1 | 7/2013 | Roh |
| 2013/0231680 A1 | 9/2013 | Diolaiti et al. |
| 2013/0245375 A1 | 9/2013 | Dimaio et al. |
| 2013/0289767 A1 | 10/2013 | Lim et al. |
| 2014/0052150 A1 | 2/2014 | Taylor et al. |
| 2014/0055489 A1 | 2/2014 | Itkowitz et al. |
| 2014/0135792 A1 | 5/2014 | Larkin et al. |
| 2014/0232824 A1 | 8/2014 | Dimaio et al. |
| 2015/0032126 A1 | 1/2015 | Nowlin et al. |
| 2015/0051733 A1 | 2/2015 | Nowlin et al. |
| 2015/0065793 A1 | 3/2015 | Diolaiti et al. |
| 2015/0150639 A1 | 6/2015 | Diolaiti et al. |
| 2015/0182287 A1 | 7/2015 | Guthart et al. |
| 2015/0297300 A1 | 10/2015 | Gomez et al. |
| 2015/0366625 A1 | 12/2015 | Tognaccini et al. |

(56) References Cited

U.S. PATENT DOCUMENTS

| | | |
|---|---|---|
| 2016/0045272 A1 | 2/2016 | Diolaiti |
| 2016/0235486 A1 | 8/2016 | Larkin |
| 2016/0242860 A1 | 8/2016 | Diolaiti et al. |
| 2016/0374767 A1 | 12/2016 | Diolaiti et al. |
| 2017/0035521 A1 | 2/2017 | Diolaiti et al. |
| 2017/0173788 A1 | 6/2017 | Diolaiti et al. |
| 2017/0209232 A1 | 7/2017 | Larkin et al. |
| 2017/0210012 A1 | 7/2017 | Larkin et al. |

FOREIGN PATENT DOCUMENTS

| | | |
|---|---|---|
| EP | 0646358 A1 | 4/1995 |
| EP | 812662 A1 | 12/1997 |
| EP | 1125557 A2 | 8/2001 |
| EP | 0732082 B1 | 9/2002 |
| EP | 1310844 A1 | 5/2003 |
| EP | 1424173 A2 | 6/2004 |
| JP | S61230895 A | 10/1986 |
| JP | H01280449 A | 11/1989 |
| JP | H04231034 A | 8/1992 |
| JP | H07184923 A | 7/1995 |
| JP | H07265321 A | 10/1995 |
| JP | H0889506 A | 4/1996 |
| JP | H08107875 A | 4/1996 |
| JP | H08132372 A | 5/1996 |
| JP | H08154321 A | 6/1996 |
| JP | H08215211 A | 8/1996 |
| JP | H08275958 A | 10/1996 |
| JP | H08299363 A | 11/1996 |
| JP | H09141580 A | 6/1997 |
| JP | H10146341 A | 6/1998 |
| JP | H11309 A | 1/1999 |
| JP | 2000500679 A | 1/2000 |
| JP | 2000300579 A | 10/2000 |
| JP | 2001000448 A | 1/2001 |
| JP | 2001061850 A | 3/2001 |
| JP | 2001104333 A | 4/2001 |
| JP | 2001202531 A | 7/2001 |
| JP | 2001287183 A | 10/2001 |
| JP | 2002103258 A | 4/2002 |
| JP | 2002287613 A | 10/2002 |
| JP | 2003053684 A | 2/2003 |
| JP | 2003300444 A | 10/2003 |
| JP | 2003339725 A | 12/2003 |
| JP | 2004105638 A | 4/2004 |
| JP | 2004223128 A | 8/2004 |
| JP | 2005110878 A | 4/2005 |
| JP | 2005135278 A | 5/2005 |
| JP | 2005303327 A | 10/2005 |
| JP | 2005334650 A | 12/2005 |
| JP | 2007029232 A | 2/2007 |
| JP | 2007090481 A | 4/2007 |
| JP | 2007508913 A | 4/2007 |
| JP | 2007531553 A | 11/2007 |
| JP | 2009006410 A | 1/2009 |
| JP | 2009012106 A | 1/2009 |
| JP | 2009039814 A | 2/2009 |
| JP | 2009525097 A | 7/2009 |
| JP | 2009537229 A | 10/2009 |
| KR | 20090111308 A | 10/2009 |
| WO | WO-9501757 A1 | 1/1995 |
| WO | WO-9507055 A1 | 3/1995 |
| WO | WO-9729690 A1 | 8/1997 |
| WO | WO-9743942 A1 | 11/1997 |
| WO | WO-9743943 A1 | 11/1997 |
| WO | WO-03061482 A1 | 7/2003 |
| WO | WO-2004014244 A2 | 2/2004 |
| WO | WO-2005037120 A1 | 4/2005 |
| WO | WO-2005039391 A2 | 5/2005 |
| WO | WO-2005043319 A2 | 5/2005 |
| WO | WO-2006079108 A1 | 7/2006 |
| WO | WO-2006091494 A1 | 8/2006 |
| WO | WO-2007005555 A2 | 1/2007 |
| WO | WO-2007030173 A1 | 3/2007 |
| WO | WO-2007047782 A2 | 4/2007 |
| WO | WO-2007088206 A2 | 8/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008094766 A2 | 8/2008 |
| WO | WO-2008103383 A1 | 8/2008 |
| WO | WO-2009034477 A2 | 3/2009 |
| WO | WO-2009037576 A2 | 3/2009 |
| WO | WO-2009044287 A2 | 4/2009 |
| WO | WO-2009158164 A1 | 12/2009 |
| WO | WO-2010039394 A1 | 4/2010 |

OTHER PUBLICATIONS

Abolmaesumi, Purang et al., "A User Interface for Robot-Assisted Diagnostic Ultrasound," IEEE Robotics and Automation Conference, 2001, pp. 1549-1554, vol. 2, IEEE.

Abolmaesumi, Purang et al., "Image Guided Control of a Robot for Medical Ultrasound," IEEE Transactions on Robotics and Automation, 2002, pp. 11-23, vol. 18—Issue 1, IEEE.

Adams, Ludwig et al., "Computer-Assisted Surgery," IEEE Computer Graphics & Applications, May 1990, pp. 43-52, vol. 10—Issue 3, IEEE Computer Society Press.

Ahlering, Thomas. E. et al., "Robotic radical prostatectomy: a technique to reduce pT2 positive margins," Urology, 2004, pp. 1224-1228, vol. 64 Issue 6, Elsevier Inc.

Alexander, Arthur D. III, "Impacts of Telemation on Modern Society," Symposium on Theory and Practice of Robots and Manipulators, Centre for Mechanical Sciences 1st CISM IFToMM Symposium, Sep 5-8, 1974, pp. 121-136, vol. 2, Springer-Verlag.

Arai, Tatsuo et al., "Bilateral control for manipulators with different configurations," IECON Inn Conference on Industrial Electronics Control and Instrumentation, Oct. 22-26, 1984, pp. 40-45, vol. 1.

Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.

Askew, Scott R. et al., "Ground control testbed for space station freedom robot manipulators," IEEE Virtual Reality Annual International Symposium, 1993, pp. 69-75, IEEE.

Azuma, Ronald T., "A Survey of Augmented Reality," Teleoperators and Virtual Environments, 1997, pp. 355-385, vol. 6—No. 4.

Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.

Banovac, Filip et al., "Liver Tumor Biopsy in a Respiring Phantom with the Assistance of a Novel Electromagnetic Navigation Device," 2002, pp. 200-207, Springer-Verlag.

Bartels, Richard H. et al., "An Introduction to Splines for use in Computer Graphics and Geometric Modeling," 1987, 6 Pages total, Morgan kaufmann publishers, Inc.

Bartels, Richard H. et al., "Solution of the Matrix Equation AX+XB+ 32 C," Communications of the ACM, 1972, pp. 820-826, vol. 15—Issue 9, ACM Press.

Baumann, Roger, "Haptic Interface for Virtual Reality Based Laparoscopic Surgery Training Environment," These No. 1734 Ecole Pholytechnique Federale de Lausanne, 1997, 104 Total Pages.

Bejczy, Antal K. et al., "Controlling Remote Manipulators through Kinesthetic Coupling," Computers in Mechanical Engineering, 1983, pp. 48-60, vol. 1—Issue 1.

Ben Gayed, M. et al., "An Advanced Control Micromanipulator for Surgical Applications," Systems Science, 1987, pp. 123-134, vol. 13.

Berkelman, Peter J. et al., "A Compact Compliant Laparoscopic Endoscope Manipulator," IEEE International Conference on Robotics and Automation, 2002, pp. 1870-1875, vol. 2, IEEE.

Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.

Berkelman, Peter J. et al., "A miniature microsurgical instrument tip force sensor for enhanced force feedback during robot-assisted

(56) References Cited

OTHER PUBLICATIONS manipulation," IEEE Transactions on Robotics and Automation, 2000, pp. 917-922, vol. 19—Issue 5, IEEE.

Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.

Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.

Bettini, A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.

Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.

Bettini, Alessandro et al., "Vision Assisted Control for Manipulation Using Virtual Fixtures," IEEE Transactions on Robotics, 2004, pp. 953-966, vol. 20—Issue 6, IEEE.

Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11.

Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.

Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.

Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.

Boctor, Emad, M. et al., "CISUS: An integrated 3D ultrasound system for IGT using a modular tracking API," Proceedings of the SPIE, 2004, pp. 247-256, vol. 5367, SPIE.

Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6—Supplement 1, Taylor & Francis Health Science.

Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science, 2001, pp. 13-22, vol. 2074, Springer.

Boctor, Emad, M. et al., "Robot-assisted 3D strain imaging for monitoring thermal ablation of liver," Annual congress of the Society of American Gastrointestinal Endoscopic Surgeons (SAGES),Emerging Technology Lunch Poster TP004, 2005, pp. 240-241.

Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.

Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.

Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.

Borovoi, A.V., "Stability of a manipulator with force feedback," Izv. AN SSSR Mekhanika Tverdogo Teal, 1990, pp. 37-45, vol. 25—Issue 1, Allerton Press, Inc.

Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.

Brown, Myron M. et al., "Advances in Computational Stereo," IEEE Transactions on Pattern Analysis and Machine Intelligence (PAMI), 2003, pp. 993-1008, vol. 25 Issue, IEEE.

Burdea, Grigore et al., "Dextrous Telerobotics with Force Feedback—an overview. Part 2: Control and Implementation," Robotica, 1991, pp. 291-298, vol. 9.

Burschka, Darius et al., "Scale-Invariant Registration of Monocular Endoscopic Images to CT-Scans for Sinus Surgery," Med Image Anal, 2004, pp. 413-421, vol. 2, Springer-Verlag.

Burschka, Darius et al., "Scale-Invariant Registration of Monocular Stereo Images to 3D Surface Models," IEEE Int. Conf. on Robots and Systems, 2004, pp. 2581-2586, vol. 3, IEEE.

Burschka, Darius et al., "Navigating Inner Space: 3-D Assistance for Minimally Invasive Surgery," Robotics and Autonomous Systems, 2005, pp. 5-26, vol. 52—Issue 1, Elsevier.

Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.

Bzostek, Andrew, "Computer-Integrated needle therapy systems: Implementation and Analysis," Computer Science, 2005, 379 pages.

Bzostek, Andrew et al., "A Testbed System for Robotically Assisted Percutaneous Pattern Therapy," Medical Image Computing and Computer-Assisted Surgery, Lecture Notes in Computer Science, 1999, pp. 1098-1107, vol. 1679, Springer.

Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes in Computer Science, 1997, pp. 299-308, vol. 1205, Springer-Verlag.

Bzostek, Andrew, "Image Guided Percutaneous Pattern Placement in Soft Tissue," The Johns Hopkins University Dept. of Computer Science: Baltimore, 1997, pp. Jan. 22, 2007.

Cadeddu, Jeffrey A. et al., "A Robotic System for Percutaneous Renal Access," The Journal of Urology, 1997, pp. 1589-1593, vol. 158—Issue 4.

Cadeddu, Jeffrey et al., "A robotic system for percutaneous renal access incorporating a remote center of motion design," Journal of Endourolog, 1998, S237, vol. 12.

Cannon, Jeremy W. et al., "Real-time three-dimensional ultrasound for guiding surgical tasks," Computer Aided Surgery, 2003, pp. 82-90, vol. 8—No. 2, John Wiley & Sons.

Cao, Caroline L., et al., "Task and motion analysis in endoscopic surgery," Submitted for Fifth Annual Symposium on Haptic Interfaces for Virtual Environment and Teleporator Systems for the Winter Meeting of ASME, 1996, pp. 1-32.

Carr, J., "Surface reconstruction in 3D medical imaging," PhD Thesis, University of Canterbury, Christchurch, New Zealand, 1996, 223 Pages.

Cash, David M. et al., "Incorporation of a laser range scanner into an image-guided surgical system," the International Society for Optical Engineering (Spie), Medical Imaging 2003: Visualization, Image-Guided Procedures, and Display; San Diego, CA, Ed. Robert L. Galloway, 2003, pp. 269-280, vol. 5029.

Chang, Jun Keun et al., "Intravascular micro active catheter for minimal invasive surgery," 1st Annual International Conference on Microtechnologies in Medicine and Biology, 2000, pp. 243-246.

Chen, Homer H. "A Screw Motion Approach to Uniqueness Analysis of Head-Eye Geometry," Computer Vision and Pattern Recognition, 1991, pp. 145-151, IEEE.

Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.

Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.

(56) References Cited

OTHER PUBLICATIONS

Choti, Michael A., "Hepatic Radiofrequency Ablation," Cancer Journal, 2000, pp. S291-S292, vol. 6—issue 4, Jones and Bartlett.
Choti, Michael A., "Surgical Management of Hepatocellular Carcinoma: Resection and Ablation," Journal of Vascular and Interventional Radiology, 2002, pp. S197-S203, vol. 13—No. 9.
Christensen, B. et al., "Model based sensor directed remediation of underground storage tanks," International Conf. on Robotics and Automation, Sacramento, CA, Apr. 1991, pp. 1377-1383, vol. 2. IEEE.
Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.
Chung, Mathew et al., "Laparascopic Radiofrequency Ablation of Unresectable Hepatic Malignancies," Surg Endosc, 2001, pp. 1020-1026, vol. 15—No. 9, Springer-Verlag.
Cleary, Kevin et al., "State of the Art in Surgical Robotics:Clinical Applications and Technology Challenges," Computer Aided Surgery, 2001 [retrieved on Feb. 24, 2002], pp. 1-26.
Cleary, Kevin et al., "State of the art surgical robotics clinical applications and technology challenges," Computer Aided Surgery, 2001, pp. 312-328, vol. 6; Part 6, John Wiley & Sons.
Cleary,K. et al., "Robotically-assisted spine nerve blocks," Radiology, 2001, 1 page, vol. 221—No. 618.
Cohn, Michael C., "Medical Robotics," http://www-bsac.eecs.berkeley.edu/ , 1996, pp. 1-8 and 4.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
D'Angelica M., "Staging Laparoscopy for Potentially Respectable Noncolorectal," Ann Surg Oncol, 2002, pp. 204-209, vol. 9—No. 2, Lippincott Williams & Wilkins.
Daniilidis, Konstantinos, Hand-Eye Calibration Using Dual Quaternions, Int. J. of Robotics Research, 2000, pp. 286-298, vol. 19—No. 3, Sage Publications, Inc.
Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, Page. 339, vol. 4—Iss. 6.
Davies, S. C.et al., "Ultrasound quantitaion of respiratory organ motion in the upper abdomen," British Journal of Radiology, 1994, pp. 1096-1102, vol. 37—Iss. 803.
De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.
Debus, Thomas et al., "Multichannel Vibrotactile Display for Sensory Substitution During Teleoperation," Proc. SPIE Telemanipulator and Telepresence Technologies VIII, 2001, pp. 42-49, vol. 4570, SPIE.
Degoulange, E. et al., "HIPPOCRATE: An intrinsically safe robot for medical applications," IEEE/RSH International Conference on Intelligent Biomedicine, 1998, pp. 959-964, vol. 2, IEEE.
Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.
Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 3217, Springer-Verlag.
Dodds, Zachary et al., "A hierarchical architecture for vision-based robotic manipulation tasks," in Proceedings of the International Conference on Vision Systems, 1999, pp. 312-330, vol. 542, Springer-Verlag.
Doggett, Stephen W., "Image Registered Real Time Intra-Operative Treatment Planning: Permanent Seed Brachytherapy," 2000, pp. 4.

Dolan, J.M. et al., "A Robot in an Operating Room: A Bull in a China Shop," 1987, pp. 1096-1097, vol. 2.
Elder, Matthew C. et al., "Specifying user interfaces for safety critical medical systems," Second Annual International Symposium on Medical Robotics and Computer Assisted Surgery, Nov. 1995, pp. 148-155.
Eldridge, B. et al., "A Remote Center of Motion Robotic Arm for Computer Assisted Surgery," Robotica, 1996, pp. 103-109, vol. 14 Issue 1.
Ellsmere, James et al., "A navigation system for augmenting laparoscopic ultrasound," Medical Image Computing and Computer-Assisted Intervention, Lecture Notes in Computer Science, 2003, pp. 184-191, Springer.
Extended European Search Report for Application No. 12847686.8 dated Jul. 27, 2015, 7 pages.
Fattal, Lischinsk, "Variational Classification for Visualization of 3D Ultrasound Data," Proceedings of the conference on Visualization, 2001, pp. 403-410, IEEE Computer Society.
Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.
Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.
Fichtinger, Gabor et al., "Robotically Assisted Percutaneous Local Therapy and Biopsy," 10th International Conference of Advance Robotics, 2001, pp. 133-151, IEEE.
Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.
Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.
Fichtinger, Gabor et al., "System for Robotically Assisted Prostate Biopsy and Therapy With intraOperative CT Guidance," Journal of Academic Radiology, 2002, pp. 60-74, vol. 9 No. 1, Elsevier.
Fisher, Scott S., "Virtual interface environment," IEEE/A1AA 7th Digital Avionics Systems Conference Ft. Worth Texas, 1986, pp. 346-350, IEEE.
Frantz D.D et al., "Accuracy assessment protocols for electromagnetic tracking systems," Physics in Medicine and Biology, 2003, pp. 2241-2251, Issue 48.
Fu, K.S. et al., "Robotics: control, sensing, vision, and intelligence," 1987, pp. 12-76 and 201-265, Ch. 2 & 5, McGraw-Hill Book Company.
Fuchs, Henry et al., "Augmented Reality Visualization for Laparoscopic Surgery," Medical Image Computing and Computer-Assisted Intervention, 1998, pp. 934-943, vol. 1496, Springer-Verlag.
Fukuda, Toshio et al., "A new method of master-slave type of teleoperation for a micro-manipulator system," IEEE Microrobots and Teleoperations Workshop, 1987, 5 pages, IEEE.
Funda, Janez, "An experimental user interface for an interactive surgical robot," In 1st International Symposium on Medical Robotics and Computer Assisted Surgery (MRCAS 94), Pittsburgh, 1994, pp. 196-201, 203.
Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.
Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.
Funda, Janez et al., "Control and evaluation of a 7-axis surgical robot for laparoscopy," IEEE Int. Conf. on Robotics and Automation, 1995, pp. 1477-1484, vol. 2, IEEE.
Funda, Janez et al., "Image-Guided Command and Control of a Surgical Robot," Proc. Medicine Meets Virtual Reality II, 1994, pp. 52-57.

(56) References Cited

OTHER PUBLICATIONS

Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.
Furuta, Katsuhisa et al., "Master slave manipulator based on virtual internal model following control concept," IEEE Intl. Conference on Robotics and Automation, 1987, pp. 567-572, vol. 1, IEEE.
Ganssle J.G.,,A Guide to Debouncing,The Ganssle Group,Jun. 2008,26 pages.
Garrett, William F. et al., "Real-Time Incremental Visualization of Dynamic Ultrasound Volumes Using Parallel BSP Trees," IEEE Proceedings Visualization, 1996, pp. 235-240, 490, IEEE.
Gee, Andrew et al., "Processing and visualizing three-dimensional ultrasound data," Journal of Radiology, 2004, pp. 186-193, vol. 77.
Gelb, Arthur et al., "Applied Optimal Estimation," 1974, 4 Pages Total.
Gennari, G. et al., "Probabilistic data association methods in visual tracking of groups," IEEE Conference on Computer Vision and Pattern Recognition, 2004, pp. I-790-1-797, vol. 1—issue. 27, IEEE.
Gigot, Jean-Francois et al., "Laparoscopic Liver Resection for Malignant Liver Tumors Prelimary Results of a Multicenter European Study," Ann Surg, 2002, pp. 90-97, vol. 236—issue 1.
Gonzales, Adriana Vilchis et al., "A System for Robotic Tele-echography," Medical Image Computing and Computer-Assisted Intervention, 2001, pp. 326-334, vol. 2208, Springer.
Green, Philip, S. et al., "Mobile telepresence surgery," 2nd Annual Intl Symposium on Med. Robotics and Computer Assisted Surgery, Maryland Nov. 1995, pp. 97-103.
Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.
Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.
Hager, Gregory D., "A Modular System for Robust Hand Eye Coordination Using Feedback from Stereo Vision," IEEE Transactions on Robotics and Automation, 1997, pp. 582-595, vol. 13—issue(4), IEEE.
Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.
Hager Gregory D. et al., "Multiple Kernel Tracking with SSD," Proceedings of the IEEE Conference on Computer Vision and Pattern Recognition (CVPR 2004), 2004, pp. I-790-I-797, vol. 1—issue 27, IEEE.
Hager, Gregory D. et al., "The XVision System: A Portable Substrate for Real Time Vision Applications," 1998, pp. 23-37, vol. 69—issue 1.
Hannaford, Blake et al., "Experimental and simulation studies of hard contact in force reflecting teleoperation," IEEE International Conference on Robotics and Automation Proceedings, 1988, pp. 584-589, vol. 1, IEEE.
Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.
Harris, S.J. et al., "A robotic procedure for transurethral resection of the prostate," Second Annual International Symposium on Medical Robotics and Computer Assisted Surgery, 1995, pp. 264-271.
Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.
Herline, Alan J. et al., "Image-Guided Surgery: Preliminary Feasibility Studies of Frameless Stereotactic Liver Surgery," Archives of Surgery, 1999, pp. 644-650, vol. 134—No. 6.
Herline, Alan J. et al., "Surface Registration for Use in Interactive," Image-Guided Liver Surgery, Computer Aided Surgery, 2000, pp. 11-17, vol. 5—No. 2.
Herman, Barry C., et al, "Telerobotic surgery creates opportunity for augmented reality surgery," Abstract No. T1F2, Telemedicine Journal and E-Health, vol. 11, Issue 2, p. 203, Apr. 2005.
Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.
Herper Matthew, "Watch a $1.5 Million Surgical Robot Play a Board Game," Forbes. Apr. 12, 2011. 2 pages, Online [Available: http://www.forbes.com/sites/matthewherper/2011/04/12/watch-a-1-5-million-surgical-robot-play-a-board-game/#587224f011f5] Accessed Jun. 7, 2016.
Hespanha J.P. et al., "What Tasks Can Be Performed with an Uncalibrated Stereo Vision System", International Journal of Computer Vision, 1999, pp. 65-85, vol. 35—issue. (1).
Hill, John W., "Telepresence surgery demonstration system," Robotics and Automation, 1994, pp. 2302-2307, vol. 3, SRI International.
Ho, S. C.et al., "Robot Assisted Knee Surgery," IEEE Engineering in Medicine and Biology Magazine, 1995, pp. 292-300, vol. 14—Iss. 3, IEEE.
Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.
Horn, Berthold K.P., "Closed-form solution of absolute orientation using unit quaternions," Journal of the Optical Society of America A, vol. 4, No. 4, pp. 629-642, Apr. 1987.
Hunter, Ian W. et al., "A teleoperated microsurgical robot and associated virtual environment for eye surgery," Presence: Teleoperators and Virtual Environments, 1993, pp. 265-280, vol. 2—No. 4, MIT Press.
Hunter, Ian W. et al., "Ophthalmic microsurgical robot and associated virtual environment," Comput. Biol. Med, 1995, vol. 25, Issue 2, pp. 173-182, Pergamon.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Hutchinson, Seth et al., "A Tutorial Visual Servo Control," IEEE Transactions on Robotics and Automation, 1996, pp. 651-670, vol. 12 issue.5, IEEE.
IEEE Systems and Software Engineering—Recommended Practice for Architectural Description of Software-Intensive Systems, IEEE Std 1471-2000, 34 pages, First Edition, Jul. 15, 2007.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Search Report and Written Opinion for Application No. PCT/US2012/064379, dated Mar. 29, 2013, 12 pages.
International Search Report and Written Opinion for Application No. PCT/US2012/064400, dated Mar. 27, 2013, 10 pages.
Intuitive Surgical, Inc., "Intuitive Surgical daVinci API v5.0 Reference Manual," generated Jul. 17, 2006, 149 pages.
Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.
Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.
Johns Hopkins University and Intuitive Surgical, Inc., "System Requirements for the Surgical Assistant Workstation," Rev. 2, Jan. 29, 2007, 17 pages.
Jones, Daniel B. et al., "Next generation 3D videosystems may improve laprascopic task performance," Interactive Technology and the New Paradigm for Healthcare, 1995, pp. 152-160, Ch 25.

(56) References Cited

OTHER PUBLICATIONS

Joskowicz, Leo et al., "Computers in Imaging and Guided Surgery," Computing in Science and Engineering, 2001, pp. 65-72, vol. 3—Issue: 5, IEEE.
Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.
Kane, Robert A., "Intraoperative Ultrasonography, History, Current State of the Art, and Future Directions," J Ultrasound Med, 2004, pp. 1407-1420, vol. 23.
Kaplan, Irving, "Minimizing Rectal and Urinary Complications in Prostate Brachytherapy," Journal of Endourology, 2000, pp. 381-383.
Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.
Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.
Kapoor, Ankur et al., "Simple Biomanipulation Tasks with a Steady Hand Cooperative Manipulator," In Proceedings of the Sixth International Conference on Medical Image Computing and Computer Assisted Intervention—MICCAI Lecture Notes in Computer Science, 2003, vol. 1, Springer.
Kapoor, Ankur et al., "Suturing in Confined Spaces: Constrained Motion Control of a Hybrid 8-DOF Robot," Proceedings, 12th International Conference on Advanced Robotics, 2005, pp. 452-459.
Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.
Kato H., et al., "The Effects of Spatial Cues in Augmented Reality Video Conferencing," Hiroshima City University, Aug. 2001, 4 pages.
Kato H., et al. "Virtual Object Manipulation on a Table-Top AR Environment," Hiroshima City University, 2000, 9 pages.
Kavoussi, Louis R., "Laparoscopic donor nephrectomy," Kidney International, 2000, pp. 2175-2186, vol. 57.
Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.
Kazanzides, Peter et al., "Force Sensing and Control for a Surgical Robot," Int. Conference on Robotics and Automation, May 1992, Nice, France; pp. 612-617, vol. 1, IEEE.
Kazerooni, H. , "Human Extenders," ASME J. Dynamic Systems, Measurements and Control, 1993, pp. 281-290, vol. 115 No. 2(B).
Kazerooni, H., "Design and analysis of the statically balanced direct-drive robot manipulator," Robotics and Computer-Integrated Manufacturing, 1989, pp. 287-293, vol. 6, Issue 4.
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kilmer, R. D. et al., "Watchdog safety computer design and implementation," RI/SME Robots 8 Conference, Jun. 1984, pp. 101-117.
Kim, Won S. et al., "Active compliance and damping in telemanipulator control," Jet Propulsion Laboratory New technology Report, 1991, pp. 1-14a, vol. 15—Issue 4, JPL & NASA Case No. NPO-1796917466, Item 40.
Kitagawa, Masaya et al., "Effect of Sensory Substitution on Suture Manipulation Forces for Surgical Teleoperation," 12th Annual Medicine Meets Virtual Reality Conference, 2005, 8 pages.

Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.
Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.
Komada, Satoshi et al., "Bilateral robot hand based on estimated force feedback," IEEE Proceedings IECON 87 Cambridge MA, Nov. 3-6, 1987, pp. 602-607, vol. 2, IEEE.
Kon, Ryan et al., "An open-source ultrasound calibration toolkit," Medical Imaging Ultrasonic Imaging and Signal Processing, 2005, pp. 516-523, vol. 5750, SPIE.
Korein James U. et al., "A Configurable System for Automation Programming and Control," IEEE Conf. on Robotics and Automation. San Francisco, 1986, pp. 1871-1877, vol. 3, IEEE.
Kosugi, Yukio et al., "An articulated neurosurgical navigation system using MRI and CT Images," IEEE Transactions on Biomedical Engineering, 1988, pp. 147-152, vol. 35—Issue 2, IEEE.
Kragic D. et al., "Human-Machine Collaborative Systems for Microsurgical Applications," International Symposium on Robotics Research, 2005, pp. 731-741, vol. 24—Issue 9, Sage Publications.
Kruchten, Philippe B., "The 4+1 View Model of Architecture," IEEE Software, vol. 12, Issue 6, pp. 42-50, Nov. 1995.
Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention—Part , Lecture Notes in Computer Science, 2002, pp. 9-16, vol. 2488, Springer Verlag.
Kumar, Rajesh, "An Augmented Steady Hand System for Precise Micromanipulation," 2001, 109 pages.
Kumar, Rajesh et al., "An Augmentation System for Fine Manipulation," Proceedings of the Third International Conference on Medical Image Computing and Computer-Assisted Intervention, Lecture Notes in Computer Science, 2000, pp. 956-964, vol. 1935, Springer Verlang.
Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes in Computer Science, 2001, pp. 1417-1418, vol. 2208, Springer Verlang.
Kumar, Rajesh et al., "Experiments with a Steady Hand Robot in Constrained Compliant Motion and Path Following", 1999, pp. 92-97, IEEE.
Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.
Kumar, Rajesh et al., "Preliminary experiments in robot/human microinjection," IEEE/RSJ International Conference on Intelligent Robots and Systems, 2003, pp. 3186-3191, vol. 3, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
Lacroute, Philippe et al., "The VolPack Volume Rendering Library," 2003, pp. 4.
Lacroute, Philippe G., "Fast Volume Rendering Using a Shear-Warp Factorization of the Viewing Transformation PhD Thesis," Computer Science, Stanford, California, 1995, 236 Pages.
Lang, Samuel J., Xvision 2—A Framework for Dynamic Vision. Masters Thesis, Computer Science, Johns Hopkins University, Baltimore, 2001, pp. 1-49.
Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.
Lau, William W. et al., "Stereo-Based Endoscopic Tracking of Cardiac Surface Deformation," Proceedings of Seventh International Conference on Medical Image Computing and Computer-

(56) References Cited

OTHER PUBLICATIONS

Assisted Intervention (MICCAI), Lecture Notes in Computer Science, 2004, pp. 494-501, vol. 2, Springer Verlag.

Lavonius, Maija I. et al., "Staging of Gastric Cancer: A Study with Spiral Computed Tomography, Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.

Lawson, Charles L. et al., "Linear least squares with linear inequality constraints Solving Least Squares Problems," 1974, pp. 158-173, Prentice Hall Inc.

Lazarevic, Zoran, "Feasibility of a Stewart Platform with Fixed Actuators as a Platform for CABG Surgery Device," 1997, 45 pages, Master's Thesis Columbia University Department of Bioengineering.

Lee Jr, Fred T. et al., "CT-monitored percutaneous cryoablation in a pig liver model," Radiology, 1999, pp. 687-92, vol. 211(3).

Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.

Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.

Levoy, Marc, "Display of Surfaces from Volume Data," IEEE Computer Graphics and Applications, 1988, pp. 29-37, vol. 8—Iss. 3, IEEE.

Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.

Li, Ming and Russell H. Taylor, "Performance of surgical robots with automatically generated spatial virtual fixtures," IEEE International Conference on Robotics and Automation, Barcelona, Spain, Apr. 2005, pp. 217-222.

Li, Ming et al, "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.

Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.

Li, Ming et al., "Recognition of Operator Motions for Real-Time Assistance using Virtual Fixtures," IEEE, HAPTICS 2003, 11th Symposium on Haptic Interfaces for Virtual Environment and Teleoperator Systems, Mar. 22-23, 2003, pp. 125-131, IEEE.

Li, Ming, "Intelligent Robotic Surgical Assistance for Sinus Surgery," Ph.D. Dissertation, Computer Science, Johns Hopkins University, Baltimore, 2005, 229 pages.

Loser, Michael H. et al., "A New Robotic System for Visually Controlled Percutaneous Interventions under CT Fluoroscopy," Medical Image Computing and Computer-Assisted Interventions,Lecture Notes in Computer Science, 2000, pp. 887-896, vol. 1935, Springer Verlag.

Loser, Michael H. et al., "Visual servoing for automatic and uncalibrated percutaneous procedures," SPIE Medical Imaging, 2000, pp. 270-281, vol. 3976, SPIE.

Madhani, Akhil J., "Design of Teleoperated Surgical Instruments for Minimally Invasive Surgery," Feb. 1998, pp. 1-251.

Maehara, S. et al., "Laparoscopy-Assisted Hepatectomy Using the Endoclose," Surg Endosc, 2002, pp. 1362-1365, vol. 16(9), Springer Verlag.

Maier, Georg, E. et al., "A Dynamically Configurable General Purpose Automation Controller," Proceedings of IFAC/IFIP Symp. on Software for Computer Control, 1986, pp. 47-52, Pergamon Press.

Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.

Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. by Lippincott Williams & Wilkins, Philadelphia, 2004, pp. 26-31.

Masamune K., et al., "Development of a MRI Compatible Needle Insertion Manipulator for Stereotactic Neurosurgery," Journal of Image Guided Surgery, 1995, vol. 1, pp. 242-248.

Masamune, Ken et al., "Development of a MRI Compatible Needle Insertion Manipulator for Stereotactic Neurosurgery," Image Guid Surg, 1995, pp. 165-172.

Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.

Masamune, Ken et al., "System for Robotically Assisted Percutaneous Procedures With Computed Tomography Guidance," Journal of Computer-Assisted Surgery, 2001, pp. 370-383, vol. 6—No. 6, Wiley-Liss, Inc.

Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.

Massie, Thomas H. et al., "The Phantom Haptic Interface: A Device for Probing Virtual Objects," Proceedings of the ASME Winter Annual Meeting, Symposium on Haptic Interfaces for Virtual Environment and Teleoperator Systems, 1994, 7 pages.

Mayer, Hermann et al., "Skill Transfer and Learning by Demonstration in a Realistic Scenario of Laparoscopic Surgery," International Conference on Humanoids, 2003, 17 pages, IEEE.

Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.

Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes in Computer Science, 2001, pp. 343-350, vol. 2208, Springer-Verlag.

Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.

Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.

Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.

Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.

Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.

(56) References Cited

OTHER PUBLICATIONS

Mitsuishi, Mamoru et al., "Remote Ultrasound Diagnostic System," Conf. on Robotics and Automation, 2001, pp. 1567-1574, vol. 2, IEEE.

Mourgues, Fabien et al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes in Computer Science, 2002, pp. 25-34, vol. 2488, Springer-Verlag.

Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.

Nakakura, Eric K et al., "Hepatocellular Carcinoma: Current Management Recommendations," Advances on Oncology, 2000, pp. 12-18, vol. 16—No. 2.

Neisius B. et al., "Robotic manipulator for endoscopic handling of surgical effectors and cameras," 1st Intl. Symposium on Medical Robotics and Computer Assisted Surgery, 1994, pp. 169-175, vol. 2.

Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.

Nelson, Thomas, R. et al., "Three-dimensional ultrasound imaging," Ultrasound in Medicine & Biology, 1998, pp. 1243-1270, vol. 24—No. 9, Elsevier.

Ng, W.S. et al., "Robotic Surgery, a First-Hand Experience in Transurethral Resection of the Prostate," IEEE Engineering in Medicine and Biology, Mar. 1993, pp. 120-125, vol. 12—Issue 1, IEEE.

Novotny Paul M. et al., "Tool Localization in 3D Ultrasound Images," Medical Image Computing and Computer-Assisted Intervention, 2003, pp. 969-970, vol. 2879, Springer.

Office Action dated Sep. 3, 2014 for Japanese Application No. JP20120503535 filed Mar. 26, 2010.

Office Action dated Jan. 26, 2015 for Japanese Application No. 20130186992 filed Sep. 10, 2013, 9 pages.

Office Action dated Dec. 10, 2015 for Chinese Application No. 201280055123.4 filed Nov. 9, 2012, 19 pages.

Office Action dated Jun. 12, 2015 for Japanese Application No. 20130186992 filed Sep. 10, 2013, 8 pages.

Ohbuchi, Ryutarou et al., "Incremental Volume Reconstruction and Rendering for 3D Ultrasound Imaging," The International Society of Optical Engineering, 1992, pp. 312-323, vol. 1808, SPIE.

Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.

Patriciu Alexandru et al., "Motion-based robotic instrument targeting under c-arm fluoroscopy," Medical Image Computing and Computer-Assisted Interventions, 2000, pp. 988-998, vol. 1935, Springer.

Paul, Howard A. et al., "Development of a Surgical Robot for Cementless Total Hip Arthroplasty," Clinical Orthopaedics, Dec. 1992, pp. 57-66, vol. 285.

PCT/US07/71850 International Search Report and Written Opinion of the International Searching Authority, dated Feb. 13, 2009, 9 pages.

PCT/US09/46234 International Search Report and Written Opinion of the International Searching Authority, dated Sep. 9, 2009, 13 pages.

PCT/US09/56078 International Search Report and Written Opinion of the International Searching Authority, dated Jan. 20, 2010, 12 pages.

PCT/US10/28886 International Search Report and Written Opinion of the International Searching Authority, dated Jul. 6, 2010, 11 pages.

PCT/US10/28897 International Search Report and Written Opinion of the International Searching Authority, dated Jul. 19, 2010, 16 pages.

PCT/US10/38246 International Search Report and Written Opinion of the International Searching Authority, dated Sep. 14, 2010, 17 pages.

PCT/US2011/036109 International Search Report and Written Opinion of the International Searching Authority, dated Oct. 19, 2011, 16 pages.

PCT/US2011/036109 Invitation to Pay Additional Fees and Partial International Search Report, dated Aug. 18, 2011, 5 pages.

Podnos, Yale, D. et al., "Laparoscopic Ultrasound with Radiofrequency Ablation in Cirrhotic Patients with Hepatocellular Carcinoma," Am Surg, 2001, pp. 1181-1184, vol. 67—No. 12.

Pose—definition from Merriam Webster Dictionary, 4 pages, [online], [retrieved on Apr. 3, 2015]. Retrieved from the Internet:< URL: http://www.merriam-webster.com/dictonary/pose>.

Posture—definition from Merriam Webster Dictionary, 4 pages, [online], [retrieved on Apr. 3, 2015]. Retrieved from the Internet:< URL: http://www.merriam-webster.com/dictonary/posture>.

Poulose P. K et al., "Human vs Robotic Organ Retraction During Laparoscopic Nissen Fundoplication," Surgical Endoscopy, 1999, pp. 461-465, vol. 13, Springer-Verlag.

Prager Richard et al., "Practical segmentation of 3D ultrasound," In Proceedings of Medical Image Understanding and Analysis, 1999, pp. 161-164.

Prager Richard et al., "Rapid Calibration for 3D Freehand Ultrasound," Ultrasound in Medicine and Biology, 1998, pp. 855-869, vol. 24—No. 6, Elsevier.

Prasad, Srinivas K. et al., "A minimally invasive approach to pelvic osteolysis," 2002, in Proc. Computer-Assisted Orthopaedic Surgery (CAOS), pp. 349-350.

Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI,Lecture Notes in Computer Science, 2003, pp. 279-286, vol. I, Springer.

Preising, B. et al., "A Literature Review: Robots in Medicine," IEEE Engineering in Medicine and Biology, 1991, pp. 13-22, 71, vol. 10—Issue 2, IEEE.

Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.

Ramey, Nicholas A., "Stereo-Based Direct Surface Tracking with Deformable Parametric Models," 2003, 104 Pages Total.

Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.

Ratner, Lloyd E. et al, "Laparoscopic live donor nephrectomy removes disincentives to live donation," Transplantation, 1997, pp. 3402-3403, vol. 29—Issue 8, Elsevier.

Ratner, Lloyd E. et al., "Laparoscopic live donor nephrectomy," Transplantation, 1995, pp. 1047-1049.

Rau, Beate, M. eta al., "Is There Additional Information From Laparoscopic Ultrasound in Tumor Staging", Digestive Surgery, 2002, pp. 479-483, vol. 19—No. 6.

Rockall, Timothy A., "The da Vinci Telerobotic Surgical System," Chapter 8 in Primer of Robotic & Telerobotic Surgery, Eds. Garth H. Ballantyne et al., Pub. by Lippincott Williams & Wilkins, Philadelphia, 2004, pp. 57-60.

Rohling, Robert et al., "Three-dimensional spatial compounding of ultrasound images," Medical Image Analysis, 1996, pp. 177-193, vol. 1—No. 3, Oxford University Press.

Rohling, Robert N. et al., "Radial basis function interpolation for 3-d ultrasound," CUED/F-INFENG/TR 327, Cambridge University, Jul. 1998, 28 Pages.

Rosen, Jacob et al., "The BlueDRAGON—A System for Measuring the Kinematics and the Dynamics of Minimally Invasive Surgical Tools In-Viva," Proceedings of the 2002 IEEE International Conference on Robotics 8 Automation, 2002, pp. 1876-1881, IEEE.

Rosenberg, Louis B., "Human interface hardware for virtual laparoscopic surgery," Proceedings of the Interactive Technology and the New Paradigm for Healthcare, 1995, pp. 322-325, Amsterdam: IOS Press.

(56) References Cited

OTHER PUBLICATIONS

Rosenberg, Louis B., "Virtual Fixtures: Perceptual Tools for Telerobotic Manipulation," IEEE Virtual Reality International Symposium, 1993, pp. 76-82, IEEE.
Rothbaum Daniel L. et al., "Robot-assisted stapedotomy: micropick fenestration of the stapes footplate," Otolaryngology—Head and NeckSurgery, 2002, pp. 417-426, vol. 127.
Rothbaum Daniel L. et al., "Task Performance in stapedotomy: Comparison between surgeons of different experience levels," Otolaryngology—Head and Neck Surgery, 2003, pp. 71-77, vol. 128—No. 1.
Roy, Jaydeep, "Advances in the design, analysis and control of force controlled robots," Master's Thesis, Mechanical Engineering, Johns Hopkins University, Baltimore, 2001, 210 Pages.
Sakas, Georgios et al., "Extracting surfaces from fuzzy 3D-Ultrasound data," Proceedings of the 22nd annual conference on Computer graphics and interactive techniques, 1995, pp. 465-474.
Salcudean, Septimiu E. et al., "A Robot System for Medical Ultrasound," 9th International Symposium of Robotics Research (ISRR'99), 1999, pp. 195-202.
Santambrogio, R. et al., "Ultrasound-Guided Interventional Procedures of the Liver During Laparoscopy: Technical Considerations," Surg Endosc, 2002, pp. 349-354, Springer-Verlag.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Sastry, Shankar, http://robotics.eecs.berkeley.edu, Nov. 1, 1995, Total 8 pages.
Sastry, Shankar, "MilliRobotics in Minimally Invasive Telesurgery," Internet, http://robotics.eecs.berkeley.edu, 1996, 8 pages.
Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.
Schorr, Oliver et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes in Computer Science, 2000, pp. 979-978, vol. 1935, Springer.
Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.
Schweikard, Achim et al., "Motion Planning in Stereotaxic Radiosurgery," IEEE Transactions on Robotics and Automation, 1993, pp. 909-916, vol. 1, IEEE.
Scott, D.J., "Accuracy and Effectiveness of Laparoscopic vs. Open Hepatic Radiofrequency Ablation," Surg Endosc, 2001, pp. 349-354, vol. 16—No. 2, Springer.
Shahram, Payandeh, et al., "On Application of Virtual Fixtures as an Aid for Telemanipulation and Training," IEEE 10th Symposium on Haptic Interfaces for Virtual Environment and Teleoperator systems, Mar. 24-25, 2002, pp. 18-23, IEEE.
Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.
Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.
Solomon, Stephen B. et al., "CT Guided Robotic Needle Biopsy: A Precise Sampling Method Minimizing Radiation Exposure to the Physician, Radiology," 2002, pp. 277-282, vol. 225.
Solomon, Stephen B. et al., "Robotically Driven Interventions: A Method of Using CT Fluoroscopy without Radiation Exposure to the Physician," Radiology, 2002, pp. 277-282, vol. 225.

Solus—3D web site: Last updated Jun. 24, 1999; downloaded Jul. 5, 2007.
Sommer, Graham et al., "Liver tumors: utility of characterization at dual frequency US," Radiology, 1999, pp. 629-636, vol. 211—No. 3.
Steele, Micah R. et al., "Shared control between human and machine: using a haptic steering wheel to aid in land vehicle guidance," Human Factors and Ergonomics Society 45th Annual Meeting , Minneapolis, Minnesota, 2001, pp. 1671-1675.
Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.
Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.
Stetten, George D et al., "Overlaying Ultrasound Images on Direct Vision," Journal of Ultrasound in Medicine, 2001, pp. 235-240, vol. 20—No. 3.
Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.
Stoainovici D., et al., "Robotic Telemanipulation for Percutaneous Renal Access," in 16th World Congress on Endourology, New York City, Sep. 3-6, 1998, Poster Session 17-5, p. S201.
Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.
Stoianovici, Dan et al., "Robotic for Precise Percutaneous Needle Insertion," in Thirteenth Annual Meeting of the Society for Urology and Engineering. San Diego, May 1998, pp. 4.
Stoll, Jeff, "Ultrasound-based servoing of manipulators for telesurgery," Telemanipulator and Telepresence Technologies VIII Conference, 2001, pp. 78-85, SPIE.
Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.
Suramo, I. et al., "Cranio-caudal movements of the liver, pancreas and kidneys in respiration," Acta Radiologica: Diagnosis, 1984, pp. 129-131, vol. 25, Radiological Societies.
Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.
Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA .
Taubes, Gary et al., "Surgery in Cyberspace," Discover magazine, Dec. 1994, vol. 15, issue 12, pp. 85-92.
Tavakoli, M., et al, A Force Reflective Master-Slave System for Minimally Invasive Surgery, Proc. IEEE/RSJ International Conference on Intelligent Robots and Systems, 2003, pp. 3077-3082, vol. 4, IEEE.
Taylor, Russell H., "A Perspective on Medical Robotics," Proceedings of the IEEE, vol. 94, No. 9, Sep. 2006, pp. 1652-1664.
Taylor, Russell H. "An Image-directed Robotic System for Precise Orthopaedic Surgery," IEEE Transactions on Robotics mid Automation, 1994, pp. 261-275, vol. 10—No. 3, IEEE.
Taylor, Russell H. and Christopher Nasser, "Development of a Surgical Assistant Workstation for Teleoperated Surgical Robots," NSF Proposal No. 0646678, Aug. 2006, 16 pages.
Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.
Taylor, Russell H. and Peter Kazanzides, "Medical Robotics and Computer-Integrated Interventional Medicine," Chapter 18: Bio-

(56) References Cited

OTHER PUBLICATIONS medical Information Technology, David Dagan Feng, Ed., Academic Press (Elsevier), 2008, pp. 393-416.
Taylor, Russell H. et al., "A Computational Architecture for Programmable Automation Research," Conference on Intelligent Robots and Computer Vision, 1986, pp. 438-440, vol. 726, SPIE.
Taylor, Russell H. et al., "A General Purpose Control Architecture for Programmable Automation Research," Proceedings of the Third International Symposium on Robotics, 1986, pp. 165-174, MIT Press.
Taylor, Russell, H et al., "A Steady-Hand Robotic System for Microsurgical Augmentation," International Journal of Robotics Research, 1999, pp. 1201-1210, vol. 18—No. 12, Springer-Verlag.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H. et al., "A Telerobotic System for Augmentation of Endoscopic Surgery," in IEEE Conference on Engineering in Medicine and Biology, vol. 14, 1992, pp. 1054-1056, vol. 3, IEEE.
Taylor, Russell, H et al., "AML A Manufacturing Language," The International Journal of Robotics Research, 1982, pp. 19-41, vol. 1—No. 3, Sage Publications.
Taylor, Russell H. et al., "An Image-directed Robotic System for Hip Replacement Surgery," J. Robotics Society of Japan, 1990, pp. 615-620, vol. 8—issue 5.
Taylor, Russell, H. et al., "An Integrated Robot Systems Architecture," Proceedings of the IEEE, 1983, pp. 842-856, vol. 71—Issue 7, IEEE.
Taylor, Russell H., et al., "An overview of computer-integrated surgery at the IBM Thomas J. Watson Research Center," IBM J Research and Development, 1996, pp. 163-183, vol. 40, Issue 2, IBM Corp.
Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.
Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.
Taylor, Russell H. et al., "Computer-Integrated Surgery," 1996, 8 Pages, MIT Press.
Taylor, Russell H. et al., "Medical Robotics and Computer-Integrated Surgery," Chapter 52 in Springer Handbook of Robotics, Springer, 2008, pp. 1199-1222.
Taylor, Russell H. et al., "Medical Robotics in Computer-Integrated Surgery," IEEE Transactions on Robotics and Automation, 2003, pp. 765-781, vol. 19—No. 5, IEEE.
Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.
Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.
Taylor, Russell, H et al., "The Architecture of an Integrated Robot System," First Int. Conf. on Advanced Robotics (ICAR)., 1983, pp. 389-398.
Taylor, Russell H. "Medical Robotics and Computer-Integrated Surgery," Handbook of Industrial Robotics, Second Edition, 1999, pp. 1213-1230, Chapter 65, John Wiley & Sons.
Taylor, Russell H. "Medical Robots," in Computer and Robotic Assisted Knee and Hip Surgery, 2004, pp. 54-59, Oxford Press.
Taylor, Russell H., "Robotics in Orthopedic Surgery," in Computer Assisted Orthopaedic Surgery (CAOS), L.P. Nolte and R. Ganz, Editors. 1999, Hogrefe and Huber, 1999, pp. 35-41.
Taylor, Russell H. "The Planning and Execution of Straight Line Manipulator Trajectories," IBM Journal of Research and Development, 1979, pp. 424-436, vol. 23—Issue 4.
Taylor, Russell H., "Ultrasound Assistant for a Laparoscopic Surgical Robot," NIH STTR Phase II Proposal R42-RR019159, revised May 2001, 54 pages.
Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.
Tewari, Ashutosh et al., "Technique of da Vinci Robot-Assisted Anatomic Radical Prostatectomy," Urology, 2002, pp. 569-572,vol. 60—No. 4, Elsevier.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
Toon, John, "Virtual Reality for Eye Surgery," Georgia Tech Research News, 1993, 4 Pages.
Toyama, Kentaro et al., "Incremental Focus of Attention for Robust Visual Tracking," International Journal of Computer Vision, 1999, pp. 45-63, vol. 35—No. 1, Kluwer Academic Publishers.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trivedi, Mohan M. et al., "Developing telerobotic systems using virtual reality concepts," 1993 IEEE/RSJ International Conference on Intelligent Robots and systems, 1993, pp. 352-359, vol. 1, IEEE.
Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.
Uecker, Darrin R. et al., "A Speech-Directed Multi-Modal Man-Machine Interface for Robotically Enhanced Surgery," 1994, pp. 176-183.
Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.
U.S. Appl. No. 11/583,963 Non-Final Office Action dated Jul. 9, 2009, 40 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vibet, C., "Properties of Master Slave Robots," Motor-con, 1987, pp. 309-316.
Vilchis, Adriana et al., "A New Robot Architecture for Tele-Echography," IEEE Trans. Robotics & Automation, pp. 922-926, 2003, vol. 19—No. 5, IEEE.
Viswanathan, Anand et al., "Immediate Ultrasound Calibration with Three Poses and Minimal Image Processing," MICCAI, 2004, pp. 446-454, vol. 2, Springer-Verlag.
Webster Robert J. et al., "Design Considerations for Robotic Needle Steering," International Conference on Robotics and Automation, 2005, pp. 3588-3594, IEEE.
Webster Robert J. et al "Nonholonomic Modeling of Needle Steering," The International Journal of Robotics Research, 2004, pp. 509-525, vol. 25—No. 5-6, Sage Publications.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.
Wei, Zhouping et al "Robot-assisted 3D-TRUS guided prostate brachytherapy: system integration and validation," Medical Physics, 2004, pp. 539-548, vol. 31—No. 3.
Wengert, Christian, "Camera Calibration Toolbox for Matlab," [online][retrieved on Oct. 24, 2006], Retrieved from the Internet:< url:>, 5 pages.<url:></url:></url:>.
Wilhelm, Dirk et al., "Electromagnetically Navigated Laparoscopic Ultrasound," Surg. Technol. Int, 2003, pp. 50-54, vol. 11.

(56) References Cited

OTHER PUBLICATIONS

Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.

Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.

Xu, Sheng et al., "3D Motion Tracking of Pulmonary Lesions Using CT Fluoroscopy Images for Robotically Assisted Lung Biopsy," International Society of Optical Engineering, 2004, pp. 394-402, SPIE.

Yamagata, Hitoshi, "Development of a New Display Method for Compound 3D Ultrasound Images: Fusion 3D Images From B-mode and 3D Doppler Images," 1999, pp. 43-46, vol. 70.

Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.

Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.

Yao, Jianhua et al., "Deformable registration between a statistical born density atlas and X-ray images," Second International Conference on Computer Assisted Orthopaedic Surgery, 2002, pp. 168-169.

Zacherl, Johannes et al., "Current value of intraoperative sonography during surgery for hepatic neoplasms," World J Surg, 2002, pp. 550-554, vol. 26—No. 5.

Zhang, Lunwei et al., "FBG Sensor Devices for Spatial Shape Detection of Intelligent Colonoscope," IEEE International Conference on Robotics and Automation, Apr. 2004, New Orleans, Louisiana, pp. 835-840.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

Zhang, Zhengyou, "A Flexible New Technique for Camera Calibration," 1998, pp. 1-21.

Azuma et al., "Recent Advances in Augmented Reality," IEEE Computer Graphics and Applications, Dec. 2001, 14 pages.

Lievin et al., "Stereoscopic Augmented Reality System for Computer Assisted Surgery," CARS 2001, Jun. 27-30, 2001, pp. 34-47.

Office Action dated Sep. 13, 2016 for Japanese Application No. 2014-541317 filed Nov. 9, 2012, 8 pages.

Office Action dated Oct. 12, 2018 for European Application No. 12847686.8 filed Nov. 9, 2012, 4 pages.

Office Action dated Jun. 28, 2018 for Chinese Application No. 2016108994620 filed Nov. 9, 2012, 10 pages.

APPLICATION OF FORCE FEEDBACK ON AN INPUT DEVICE TO URGE ITS OPERATOR TO COMMAND AN ARTICULATED INSTRUMENT TO A PREFERRED POSE

CROSS REFERENCE TO RELATED APPLICATIONS

This application is a divisional of U.S. application Ser. No. 13/292,760 (filed Nov. 9, 2011), now U.S. Pat. No. 9,492,927, which is a continuation-in-part to U.S. application Ser. No. 12/704,669 (filed Feb. 12, 2010), now U.S. Pat. No. 8,918,211, each of which is incorporated herein by reference.

U.S. application Ser. No. 13/292,760 (filed Nov. 9, 2011) is also a continuation-in-part to U.S. application Ser. No. 12/613,328 (filed Nov. 5, 2009), now U.S. Pat. No. 9,084,623, which is a continuation-in-part to U.S. application Ser. No. 12/541,913 (filed Aug. 15, 2009), now U.S. Pat. No. 8,903,546, each of which is incorporated herein by reference.

FIELD OF THE INVENTION

The present invention generally relates to medical robotic systems and in particular, to a method and system applying force feedback on an input device to urge its operator to command an articulated instrument to a preferred pose.

BACKGROUND

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the DA VINCI® Surgical System from Intuitive Surgical, Inc., of Sunnyvale, Calif., which is a minimally invasive robotic surgical system. The DA VINCI® Surgical System has a number of robotic arms that move attached medical devices, such as an image capturing device and Intuitive Surgical's proprietary ENDOWRIST® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Articulated instruments such as an articulated camera instrument and a plurality of articulated surgical tool instruments, which are used to perform the medical procedure, may then be inserted into a proximal end of the entry guide so as to extend out of its distal end. Thus, the entry guide accommodates a single entry aperture for multiple instruments while keeping the instruments bundled together as it guides them toward the work site.

A number of challenges arise in medical robotic systems using such a bundled unit, however, because of the close proximity of the articulated camera and tool instruments. For example, because the camera instrument has proximal articulations (e.g., joints) that are not visible from the distal tip camera view, the surgeon can lose track of the current state of such articulations when moving the camera and consequently, their available range of motion. Also, when the articulations of the camera and tool instruments are out of view of the camera and therefore, not visible to the surgeon through its captured images, the surgeon may inadvertently drive links of the tools and/or camera instruments to crash into one another while telerobotically moving the articulated instruments to perform a medical procedure. In either case, the safety of the patient may be jeopardized and the successful and/or timely completion of the medical procedure may be adversely impacted.

OBJECTS AND SUMMARY

Accordingly, one object of one or more aspects of the present invention is a medical robotic system, and method implemented therein, that urges an operator to command a preferred pose for normal mode operation of an articulated instrument, which serves as a biasing point for operator commanded movement of the articulated instrument during normal operation of the instrument.

Another object of one or more aspects of the present invention is a medical robotic system, and method implemented therein, that applies force feedback on an input device to urge its operator to command the posing of an articulated instrument to a preferred pose with smooth transition to the preferred pose.

Another object of one or more aspects of the present invention is a medical robotic system, and method implemented therein, that applies force feedback on an input device to urge its operator to command the posing of an articulated instrument to a first preferred pose and then smoothly transition to a second preferred pose according to an activation signal.

These and additional objects are accomplished by the various aspects of the present invention, wherein briefly stated, one aspect is a method for urging operator manipulation of an input device to command an articulated instrument to a preferred pose, the method comprising: generating a commanded pose of the articulated instrument in response to operator manipulation of an input device; generating first force commands for a plurality of degrees of freedom of the input device so as to be indicative of a difference between a first preferred pose and the commanded pose; and applying the first force commands to the plurality of degrees of freedom of the input device by phasing in their application according to a first activation signal.

Another aspect is a medical robotic system comprising: an input device; an articulated instrument; and a processor configured to generate a commanded pose of the articulated instrument in response to operator manipulation of the input device, generate first force commands for a plurality of degrees of freedom of the input device so as to be indicative of a difference between a first preferred pose and the modified commanded pose, and command application of the first force commands on the plurality of degrees of freedom of the input device so as to phase in their application according to a first activation signal.

Additional objects, features and advantages of the various aspects of the present invention will become apparent from the following description of its preferred embodiment, which description should be taken in conjunction with the accompanying drawings.

DETAILED DESCRIPTION

Figure 1:
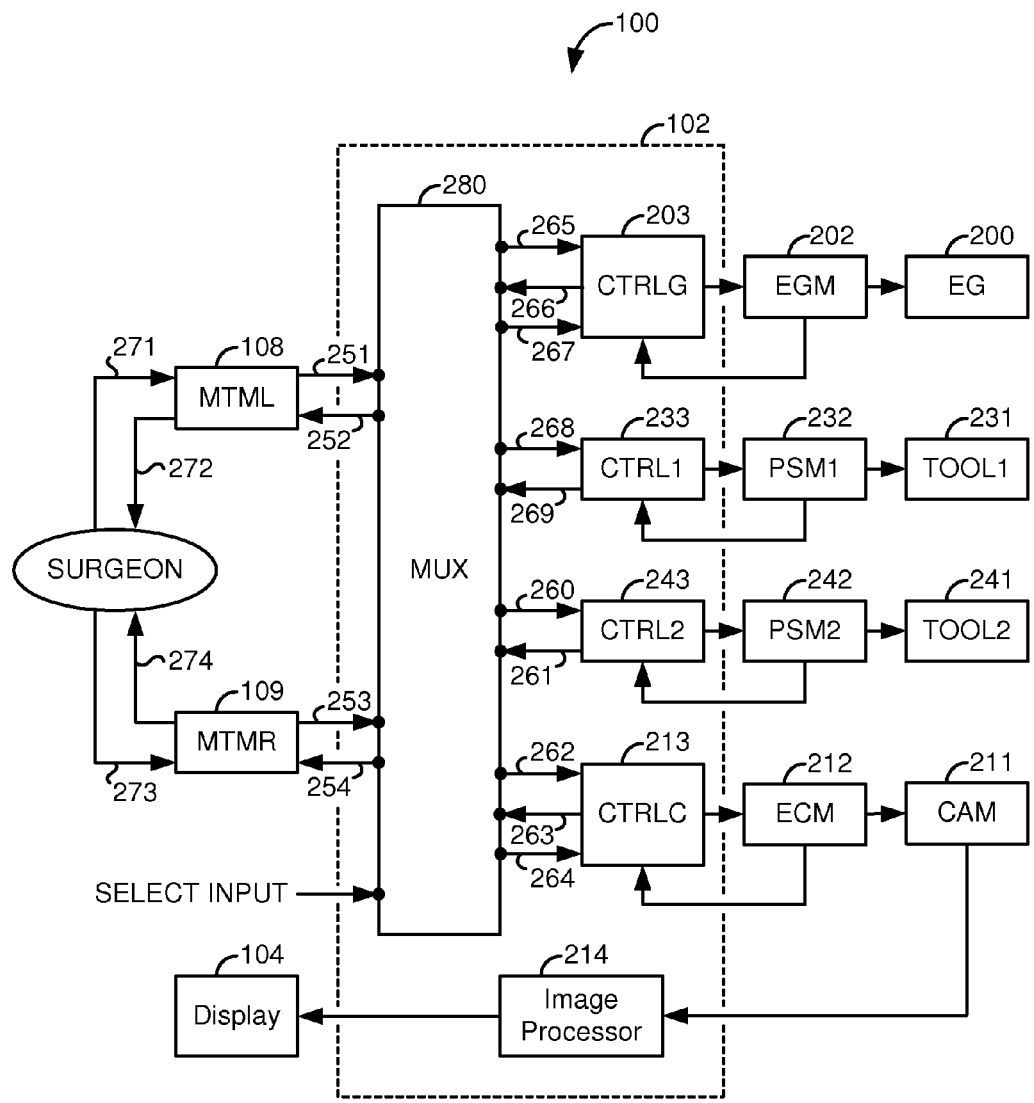
FIG. 1 illustrates a block diagram of a medical robotic system utilizing aspects of the present invention.
Figure 2:
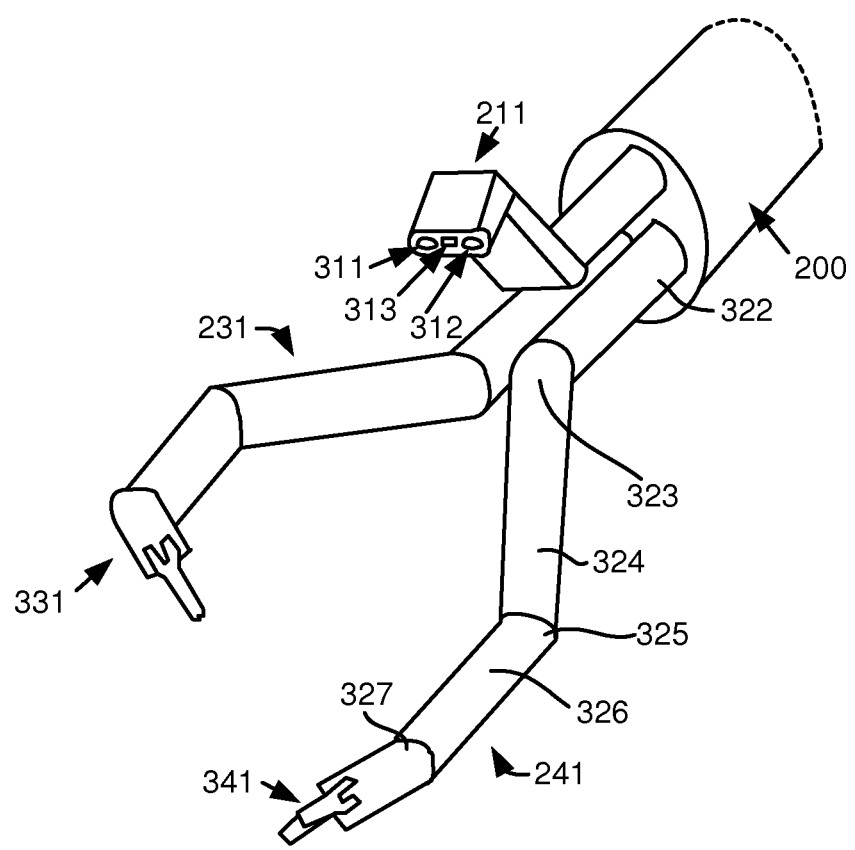
FIG. 2 illustrates a perspective view of a distal end of an entry guide with a plurality of articulated instruments extending out of it in a medical robotic system utilizing aspects of the present invention.

FIG. 1 illustrates a block diagram of a medical robotic system 100. An entry guide (EG) 200 is configured to be inserted through an entry aperture such as a minimally invasive incision or a natural body orifice in a Patient. Articulated instruments such as a first articulated surgical tool (TOOL1) 231, second articulated surgical tool (TOOL2) 241, and an articulated stereo camera (CAM) 211 may be inserted through and extend out of a distal end of the entry guide 200. As shown in FIG. 2, the camera 211 has a stereo pair of image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 200 may guide additional tools as required for performing a medical procedure at a work site in the Patient. Additional details on the articulated instruments 211, 231, 241 are provided in reference to FIGS. 3 and 4 below.

Each of the devices 231, 241, 211, 200 is manipulated and controlled by its own manipulator and controller. In particular, the articulated camera instrument 211 is manipulated by a camera manipulator (ECM) 212 which is controlled by camera instrument controller (CTRLC) 213, the first articulated surgical tool 231 is manipulated by a first tool manipulator (PSM1) 232 which is controlled by tool instrument controller (CTRL1) 233, the second articulated surgical tool 241 is manipulated by a second tool manipulator (PSM2) 242 which is controlled by tool instrument controller (CTRL2) 243, and the entry guide 200 is manipulated by an entry guide manipulator (EGM) 202 which is controlled by entry guide controller (CTRLG) 203. The controllers 203, 233, 243, 213 are implemented in processor 102 as master/slave control systems as described in reference to FIG. 6 below.

Each of the articulated instrument manipulators 232, 242, 212 is a mechanical assembly that carries actuators and provides a mechanical, sterile interface to transmit motion to its respective articulated instrument. Each articulated instrument 231, 241, 211 is a mechanical assembly that receives the motion from its manipulator and, by means of a cable transmission, propagates it to the distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams and belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

The entry guide manipulator (EGM) 202 is usable to robotically insert and retract the entry guide 200 into and out of the entry aperture. It may also be used to robotically pivot the entry guide 200 in pitch, roll and yaw relative to a longitudinal axis of the entry guide 200 about a pivot point (also referred to as a remote center "RC"). A setup arm may be used to hold and position the entry guide 200 so that its remote center RC is positioned at the entry aperture.

Two input devices 108, 109 are provided for manipulation by a Surgeon. Each of the input devices 108, 109 may be selectively associated with one of the devices 211, 231, 241, 200 so that the associated device may be controlled by the input device through its controller and manipulator. The Surgeon (or an Assistant) may perform such selection in a conventional manner, such as interacting with a menu on a Graphical User Interface (GUI), providing voice commands recognized by a voice recognition system, inputting such associations into the system 100 using an input device such as a touchpad, or interacting with special purpose buttons provided on the input devices 108, 109. Using any one of such association mechanisms, a select input is generated and provided to a multiplexer (MUX) 280, which is implemented in the processor 102. The value of the select input (e.g., combination of 1's and 0's) indicates which association (i.e., cross-switching) is selected.

For example, a first value for the select input to the multiplexer 280 places the left and right input devices 108, 109 in "tool following modes" wherein they are respectively associated with the first and second surgical tools 241, 231 so the Surgeon may perform a medical procedure on the Patient while the entry guide 200 is locked in place. In this configuration, the multiplexer 280 cross-switches to respectively connect output and input 251, 252 of the input device 108 to input and output 260, 261 of the tool controller 243; and respectively connect output and input 253, 254 of the input device 109 to input and output 268, 269 of the tool controller 233.

When the camera 211 is to be repositioned by the Surgeon, either one or both of the left and right input devices 108, 109 may be associated with the camera 211 using a second value for the select input so that the Surgeon may move the camera 211 through its controller 213 and manipulator 212. Similarly, when the entry guide 200 is to be repositioned by the Surgeon, either one or both of the left and right input devices 108, 109 may be associated with the entry guide 200 using a third value for the select input so that the Surgeon may move the entry guide 200 through its controller 203 and manipulator 202. In any case, disassociated devices are soft-locked in place by its respective controller.

The images captured by the camera instrument 211 are processed by an image processor 214 and displayed on a display screen 104 so as to provide a telepresence experience to the Surgeon, as described for example in U.S. Pat. No. 6,671,581 "Camera Referenced Control in a Minimally Invasive Surgical Apparatus," which is incorporated herein by reference. Thus, a Surgeon using the medical robotic system 100 may perform a medical procedure on the Patient by manipulating input devices 108, 109 to cause corresponding movement of associated surgical tools 231, 241 while the Surgeon views images of the work site on the display screen 104.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware distributed throughout the system.

For additional details on the construction and operation of general aspects of a medical robotic system such as described herein, see, e.g., U.S. Pat. No. 6,493,608 "Aspects of a Control System of a Minimally Invasive Surgical Apparatus," and U.S. Pat. Application Pub. No. U.S. 2008/007129 "Minimally Invasive Surgical System," which are incorporated herein by reference.

Figure 3:
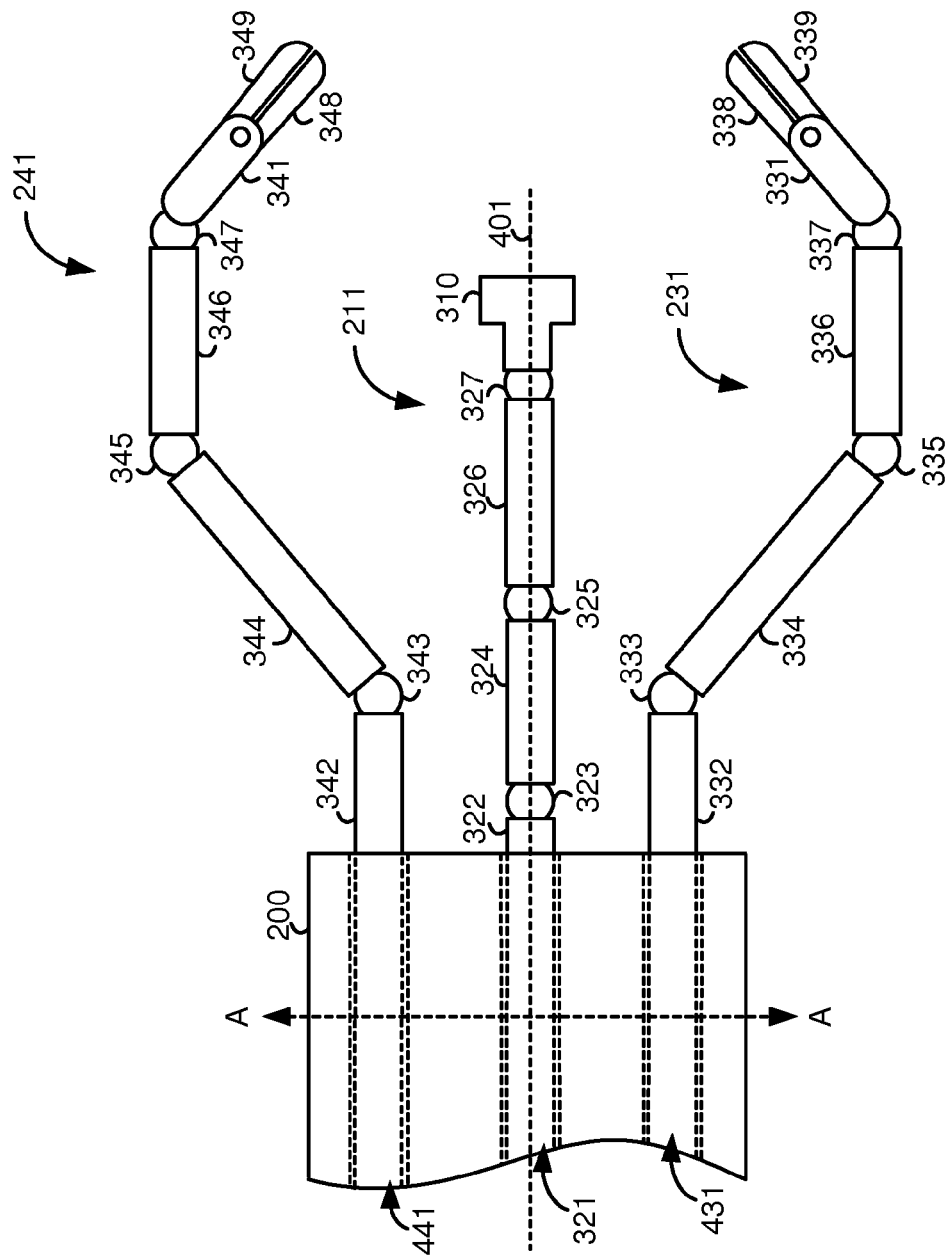
FIGS. 3-4 respectively illustrate top and right side views of articulated instruments extending out of a distal end of an entry guide in a medical robotic system utilizing aspects of the present invention.
Figure 4:
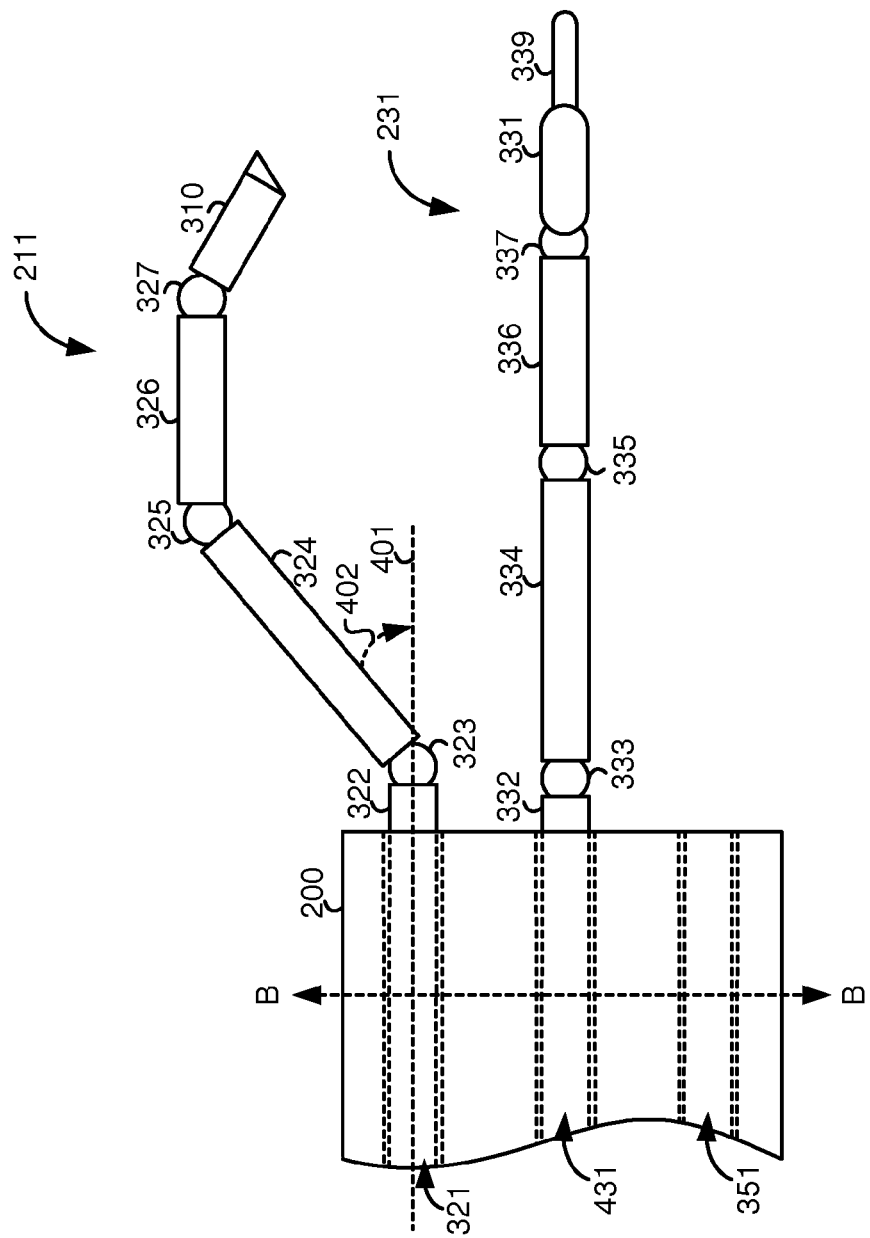

FIGS. 3-4 respectively illustrate, as examples, top and right side views of a distal end of the entry guide 200 with the articulated camera instrument 211 and articulated surgical tool instruments 231, 241 extending outward. The articulated camera 211 extends through passage 321 and the articulated surgical tools 231, 241 respectively extend through passages 431, 441 of the entry guide 200. The camera 211 includes a tip 311, first, second, and third links 322, 324, 326, first and second joint assemblies (also referred to herein simply as "joints") 323, 325, and a wrist assembly 327. The first joint assembly 323 couples the first and second links 322, 324 and the second joint assembly 325 couples the second and third links 324, 326 so that the second link 324 may pivot about the first joint assembly 323 in pitch and yaw while the first and third links 322, 326 remain parallel to each other.

The first and second joints 323, 325 are referred to as "joggle joints", because they cooperatively operate together so that as the second link 324 pivots about the first joint 323 in pitch and/or yaw, the third link 326 pivots about the second joint 325 in a complementary fashion so that the first and third links 322, 326 always remain parallel to each other. The first link 322 may also rotate around its longitudinal axis in roll as well as move in and out (e.g., insertion towards the work site and retraction from the worksite) through the passage 321. The wrist assembly 327 also has pitch and yaw angular movement capability so that the camera's tip 311 may be oriented up or down and to the right or left, and combinations thereof.

The joints and links of the tools 231, 241 are similar in construction and operation to those of the camera 211. In particular, the tool 231 includes an end effector 331 (having jaws 338, 339), first, second, and third links 332, 334, 336, first and second joint assemblies 333, 335, and a wrist assembly 337 that are driven by actuators such as described in reference to FIG. 5 (plus an additional actuator for actuating the end effector 331). Likewise, the tool 241 includes an end effector 341 (having jaws 348, 349), first, second, and third links 342, 344, 346, first and second joint assemblies 343,345, and a wrist assembly 347 that are also driven by actuators such as described in reference to FIG. 5 (plus an additional actuator for actuating the end effector 341).

Figure 5:
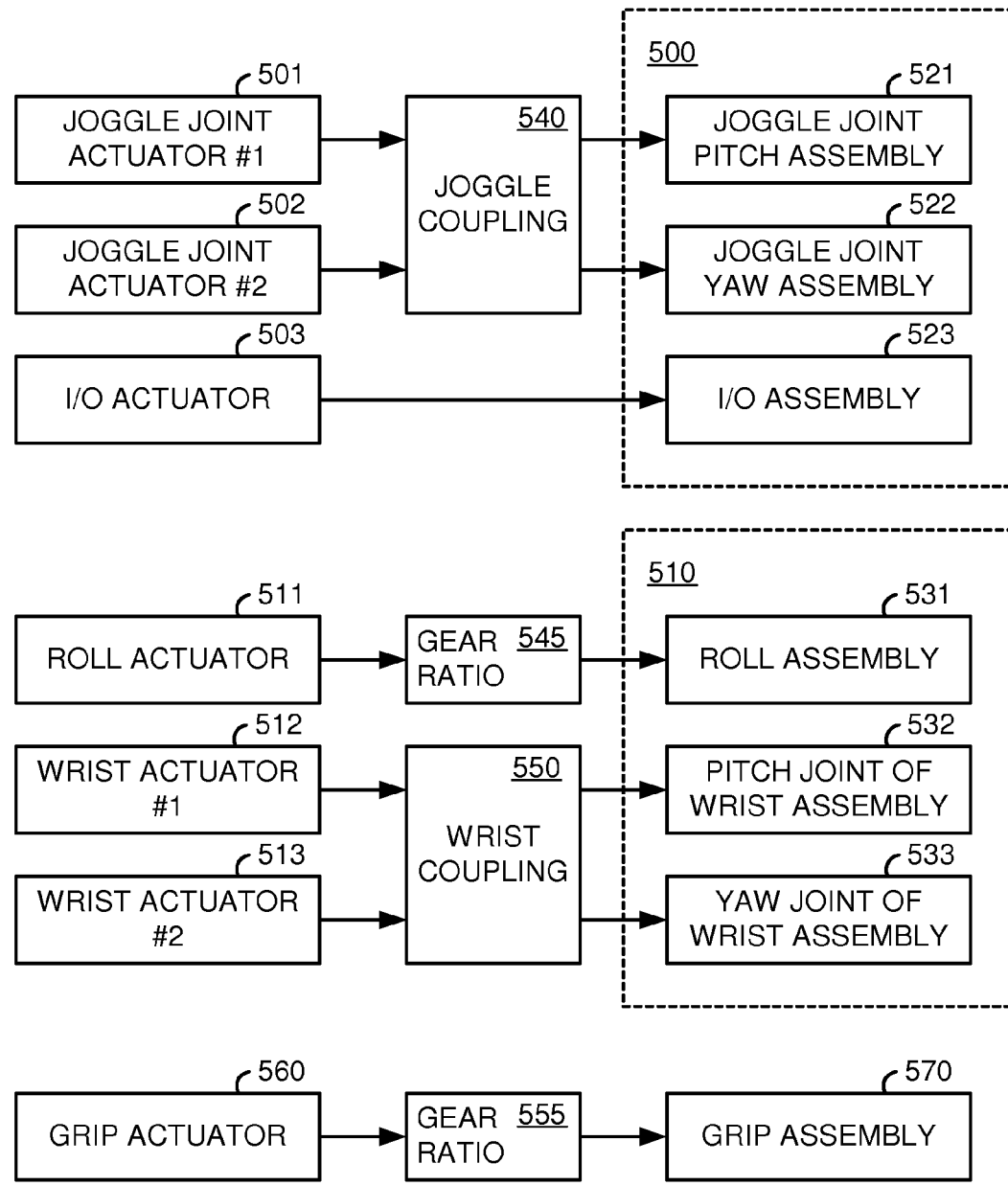
FIG. 5 illustrates a block diagram of interacting components of an articulated instrument manipulator and an articulated instrument as used in a medical robotic system utilizing aspects of the present invention.

FIG. 5 illustrates, as an example, a diagram of interacting parts of an articulated instrument (such as the articulated camera 211 and the articulated surgical tools 231, 241) and its corresponding instrument manipulator (such as the camera manipulator 212 and the tool manipulators 232, 242). Each of the instruments includes a number of actuatable assemblies 521-523, 531-533, 570 for effectuating movement of the instrument (including its end effector), and its corresponding manipulator includes a number of actuators 501-503, 511-513, 560 for actuating the actuatable assemblies.

In addition, a number of interface mechanisms may also be provided. For example, pitch/yaw coupling mechanisms 540, 550 (respectively for the joggle joint pitch/yaw and the wrist pitch/yaw) and gear ratios 545, 555 (respectively for the instrument roll and the end effector actuation) are provided in a sterile manipulator/instrument interface to achieve the required range of motion of the instrument joints in instrument joint space while both satisfying compactness constraints in the manipulator actuator space and preserving accurate transmissions of motion across the interface. Although shown as a single block 540, the coupling between the joggle joint actuators 501, 502 (differentiated as #1 and #2) and joggle joint pitch/yaw assemblies 521, 522 may include a pair of coupling mechanisms—one on each side of the sterile interface (i.e., one on the manipulator side of the interface and one on the instrument side of the interface). Likewise, although shown as a single block 550, the coupling between the wrist actuators 512, 513 (differentiated as #1 and #2) and wrist pitch/yaw joint assemblies 532, 533 may also comprise a pair of coupling mechanisms—one on each side of the sterile interface.

Both the joggle joint pitch assembly 521 and the joggle joint yaw assembly 522 share the first, second and third links (e.g., links 322, 324, 326 of the articulated camera 211) and the first and second joints (e.g., joints 322, 325 of the articulated camera 211). In addition to these shared components, the joggle joint pitch and yaw assemblies 521, 522 also include mechanical couplings that couple the first and second joints (through joggle coupling 540) to the joggle joint pitch and yaw actuators 501, 502 so that the second link may controllably pivot about a line passing through the first joint and along an axis that is latitudinal to the longitudinal axis of the first link (e.g., link 322 of the articulated camera 211) and the second link may controllably pivot about a line passing through the first joint and along an axis that is orthogonal to both the latitudinal and longitudinal axes of the first link.

The in/out (I/O) assembly 523 includes the first link (e.g., link 322 of the articulated camera 211) and interfaces through a drive train coupling the in/out (I/O) actuator 503 to the first link so that the first link is controllably moved linearly along its longitudinal axis by actuation of the I/O actuator 503. The roll assembly 531 includes the first link and interfaces through one or more gears (i.e., having the gear ratio 545) that couple a rotating element of the roll actuator 511 (such as a rotor of a motor) to the first link so that the first link is controllably rotated about its longitudinal axis by actuation of the roll actuator 511.

The instrument manipulator (e.g., camera manipulator 212) includes wrist actuators 512, 513 that actuate through wrist coupling 550 pitch and yaw joints 532, 533 of the wrist assembly (e.g., wrist assembly 327 of the articulated camera 211) so as to cause the instrument tip (e.g., camera tip 311) to controllably pivot in an up-down (i.e., pitch) and side-to-side (i.e., yaw) directions relative to the wrist assembly. The grip assembly 570 includes the end effector (e.g., end effector 331 of the surgical tool 231) and interfaces through one or more gears (i.e., having the gear ratio 555) that couple the grip actuator 560 to the end effector so as to controllably actuate the end effector.

The group of instrument joints 500 is referred to as "translational joints" because by actuation of a combination of these joints, the instrument's wrist assembly may be positioned translationally within three-dimensional space using arc compensation as needed. The group of instrument joints 510 is referred to as "orientational joints" because by actuation of these joints, the instrument's tip may be oriented about the wrist assembly.

Figure 8:
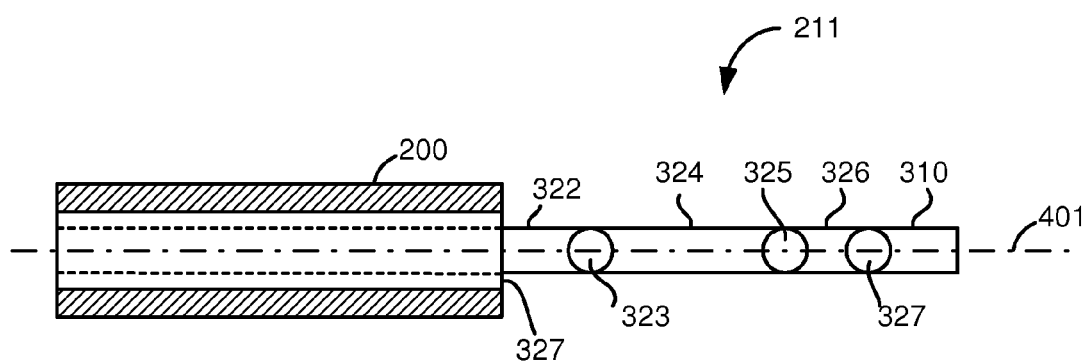
FIG. 8 illustrates a side view of an articulated instrument extending out of a distal end of an entry guide in a preferred pose for retraction back into the entry guide as used in a medical robotic system utilizing aspects of the present invention.

At various stages before, during, and after the performance of a medical procedure, there may be preferred poses for the articulated instruments 211, 231, 241 to best accomplish tasks performed at the time. For example, during normal operation, as shown in FIGS. 3 and 4, a preferred pose for each of the surgical tools 231, 241 may be an "elbow out, wrist in" pose to provide good range of motion while minimizing chances of inadvertent collisions with other instruments. Likewise, during normal operation, as shown in FIGS. 3 and 4, a preferred pose for the camera instrument 211 may be a "cobra" pose in which a good view of the end effectors 331, 341 of the surgical tool instruments 231, 241 is provided at the camera's image capturing end. As another example, when it is desired to retract an instrument back into the entry guide 200 to perform a tool exchange (i.e., exchange the instrument or its end effector for another instrument or end effector) or for reorienting the entry guide 200 by pivoting it about its remote center, a preferred pose for the instrument prior to its retraction into the entry guide 200 is a "straightened" pose wherein the links of the instrument are aligned in a straight line such as shown in FIG. 8.

Figure 6:
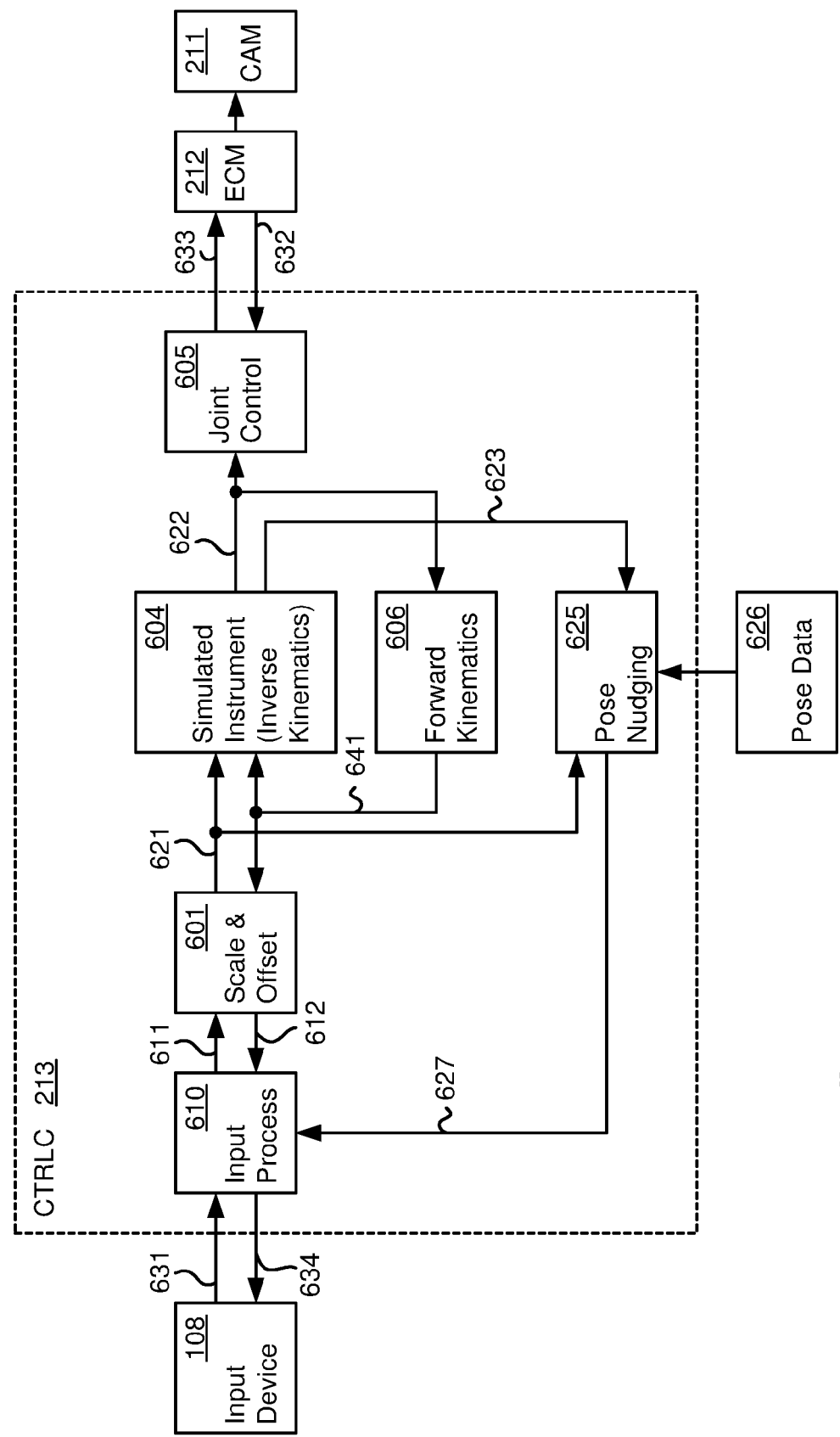
FIG. 6 illustrates a block diagram of an instrument controller for operator commanded movement of an articulated instrument in a medical robotic system utilizing aspects of the present invention.

FIG. 6 illustrates, as an example, a block diagram of the camera instrument controller (CTRLC) 213, which controls the posing (i.e., both translationally and orientationally) of the articulated camera instrument 211 as commanded by movement of the input device 108 by the Surgeon, when the input device 108 is selectively associated with the camera instrument 211 through the multiplexer 280 as previously described in reference to FIG. 1. The input device 108 includes a number of links connected by joints so as to facilitate multiple degrees-of-freedom movement. For example, as the Surgeon/operator moves the input device 108 from one position to another, sensors associated with the joints of the input device 108 sense such movement at sampling intervals (appropriate for the processing speed of the processor 102 and camera control purposes) and provide digital information 631 indicating such sampled movement in joint space to input processing block 610.

Input processing block 610 processes the information 631 received from the joint sensors of the input device 108 to transform the information into corresponding desired positions and velocities for the camera instrument 211 in its Cartesian space relative to a reference frame associated with the position of the Surgeon's eyes (the "eye reference frame") by computing joint velocities from the joint position information and performing the transformation using a Jacobian matrix and eye related information using well-known transformation techniques.

Scale and offset processing block 601 receives the processed information 611 from the input processing block 610 and applies scale and offset adjustments to the information so that the resulting movement of the camera instrument 211 and consequently, the image being viewed on the display screen 104 appears natural and as expected by the operator of the input device 108. The scale adjustment is useful where small movements of the camera instrument 211 are desired relative to larger movements of the input device 108 in order to allow more precise movement of the camera instrument 211 as it views the work site. In addition, offset adjustments are applied for aligning the input device 108 with respect to the Surgeon's eyes as he or she manipulates the input device 108 to command movement of the camera instrument 211 and consequently, its captured image that is being displayed at the time on the display screen 104.

Figure 9:
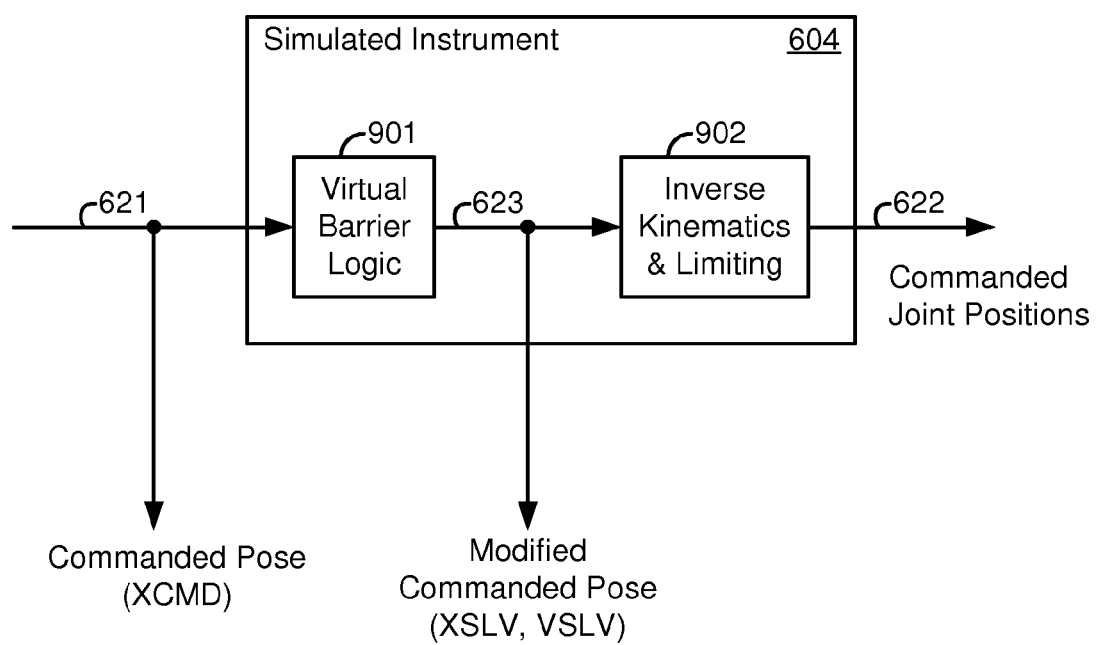
FIG. 9 illustrates a block diagram of a simulated instrument block of the instrument controller of FIG. 6 as used in a medical robotic system utilizing aspects of the present invention.

A simulated instrument block 604 transforms the commanded pose 621 of the camera instrument 211 from its Cartesian space to its joint space using inverse kinematics, limiting the commanded joint positions and velocities to avoid physical limitations or other constraints such as avoiding harmful contact with tissue or other parts of the Patient, and applying virtual constraints that may be defined to improve the performance of a medical procedure being performed at the time by the Surgeon using the medical robotic system 100. In particular, as illustrated in FIG. 9, the commanded pose 621 may be modified by virtual barrier logic 901 (described in more detail in reference to FIG. 15 below) which implements a virtual constraint on the commanded pose 621 to generate a modified commanded pose 623. Inverse kinematics and limiting block 902 then converts the modified commanded pose 623 from instrument Cartesian space to instrument joint space and limits the joint position and/or velocity to physical limitations or other constraints associated with or placed on the joints of the articulated camera instrument 211.

The output 622 of the simulated instrument block 604 (which includes a commanded value for each joint of the camera instrument 211) is provided to a joint control block 605 and a forward kinematics block 606. The joint controller block 605 includes a joint control system for each controlled joint (or operatively coupled joints such as "joggle joints") of the camera instrument 211. For feedback control purposes, sensors associated with each of the controlled joints of the camera instrument 211 provide sensor data 632 back to the joint control block 605 indicating the current position and/or velocity of each joint of the camera instrument 211. The sensors may sense this joint information either directly (e.g., from the joint on the camera instrument 211) or indirectly (e.g., from the actuator in the camera manipulator 212 driving the joint). Each joint control system in the joint control block 605 then generates torque commands 633 for its respective actuator in the camera manipulator 212 so as to drive the difference between the commanded and sensed joint values to zero in a conventional feedback control system manner.

The forward kinematics block 606 transforms the output 622 of the simulated instrument block 604 from the camera instrument's joint space back to Cartesian space relative to the eye reference frame using forward kinematics of the camera instrument 211. The output 641 of the forward kinematics block 606 is provided to the scale and offset processing block 601 as well as back to the simulated instrument block 604 for its internal computational purposes.

The scale and offset processing block 601 performs inverse scale and offset functions on the output 641 of the forward kinematics block 606 before passing its output 612 to the input processing block 610 where an error value is calculated between its output 611 and input 612. If no limitation or other constraint had been imposed on the input 621 to the simulated instrument block 604, then the calculated error value would be zero. On the other hand, if a limitation or constraint had been imposed, then the error value is not zero and it is converted to a torque command 634 that drives actuators in the input device 108 to provide force feedback felt by the hands of the Surgeon. Thus, the Surgeon becomes aware that a limitation or constraint is being imposed by the force that he or she feels resisting his or her movement of the input device 108 in that direction.

A pose nudging block 625 is included in the controller 213 to generate a nudging force command 627 which is provided to the input processing block 610. The input processing block 610 then converts the nudging force command 627 into motor torques so that the commanded nudging force is felt by the Surgeon on the input device 108 in a manner that urges the Surgeon to command the pose of the camera instrument 211 to a preferred pose provided in pose data 626.

For the camera instrument 211, there may be at least two preferred poses. During normal mode operation, such as when the Surgeon is performing a medical procedure on a Patient, the preferred pose for the camera instrument 211 is the "cobra" pose shown in FIGS. 3 and 4. Looking downward at the "cobra" pose in FIG. 3, all links 322, 324, 326 of the camera instrument 211 are aligned with the longitudinal axis 401 of the first link 322 so that they have maximum available range of lateral motion and provide a reference for the main insertion direction of the camera instrument 211. Further, the joggle joints 323, 325 are "joggled up", as shown in FIG. 4, so that the third link 326 is displaced a distance above the longitudinal axis 401 and the wrist assembly 327 is rotated at a negative pitch angle so that the camera tip 311 is oriented downwards at an angle so that the camera is preferably viewing the center of a workspace for the end effectors 331 and 341 of tool instruments 231 and 241, which are also extending out of the distal end of the entry guide 200 at the time. In this case, the Surgeon is preferably allowed to freely move the camera 211 forward and backward in the input/output (I/O) direction along the longitudinal axis 401 so that the camera 211 may better view the end effectors 331, 341 as they move away from and back towards the distal end of the entry guide 200 during their use.

Figure 7:
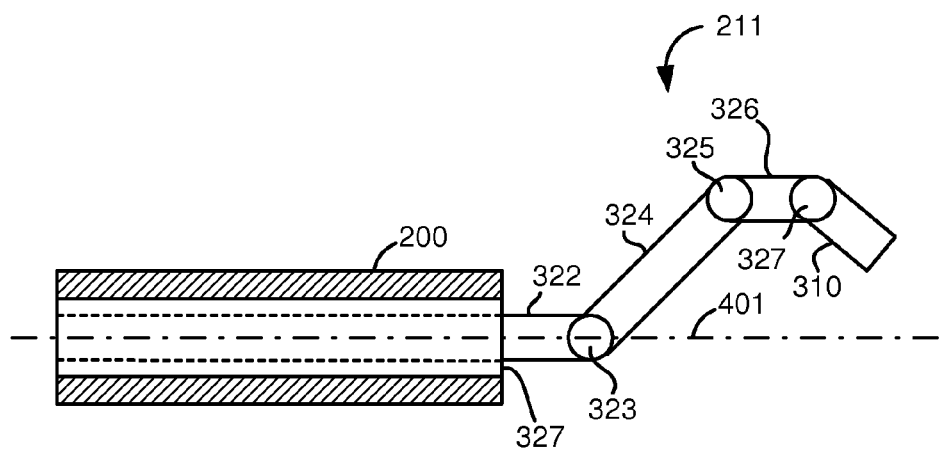
FIG. 7 illustrates a side view of an articulated instrument extending out of a distal end of an entry guide in a preferred pose for normal operation as used in a medical robotic system utilizing aspects of the present invention.

During retraction mode, the preferred pose for the camera instrument 211 is the "straightened" pose. FIGS. 7 and 8 respectively illustrate simplified side views of the camera instrument 211 in the "cobra" and "straightened" poses. To go from the "cobra" pose to the "straightened" pose, the joggle joints 323, 325 rotate link 324 until it is aligned with the longitudinal axis 401 of the first link 322. Since the link 326 is always parallel to the first link 322 due to operation of the joggle joints 323, 325, when the link 324 is aligned with the longitudinal axis 401, the link 326 also is aligned with the longitudinal axis 401. Meanwhile, the wrist joint 327 also rotates the camera tip 311 until its central axis also aligns with the longitudinal axis 401.

Figure 10:
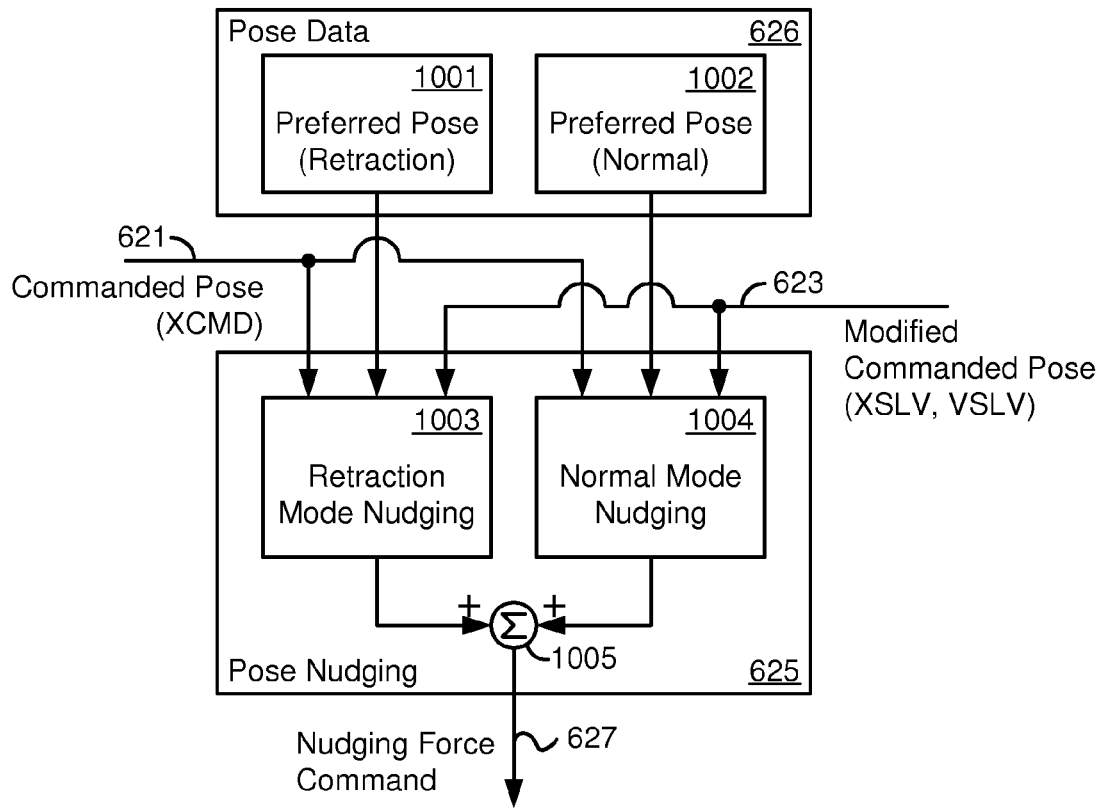
FIG. 10 illustrates a block diagram of pose data and pose nudging blocks of the instrument controller of FIG. 6 as used in a medical robotic system utilizing aspects of the present invention.

FIG. 10 illustrates, as an example, a block diagram of the pose nudging block 625 and its coupling to the pose data block 626. In this example, the pose data block 626 comprises data stored in a non-volatile memory which is accessible to the processor 102. The stored data for the camera instrument 211 includes data for the "straightened" pose 1001 which is used for retraction of the camera instrument 211 and data for the "cobra" pose 1002 which is used during normal mode operation of the camera instrument 211.

The pose nudging block 625 comprises a retraction mode nudging block 1003, a normal mode nudging block 1004, and a summing node 1005. A key feature of the retraction and normal mode nudging blocks 1003 and 1004 is that nudging force commands from one is phased in while nudging force commands from the other is being phased out during a transition period. A more detailed description of the retraction mode nudging block 1003 is described in reference to FIG. 12 below and a more detailed description of the normal mode nudging block 1004 is described in reference to FIG. 13.

Figure 12:
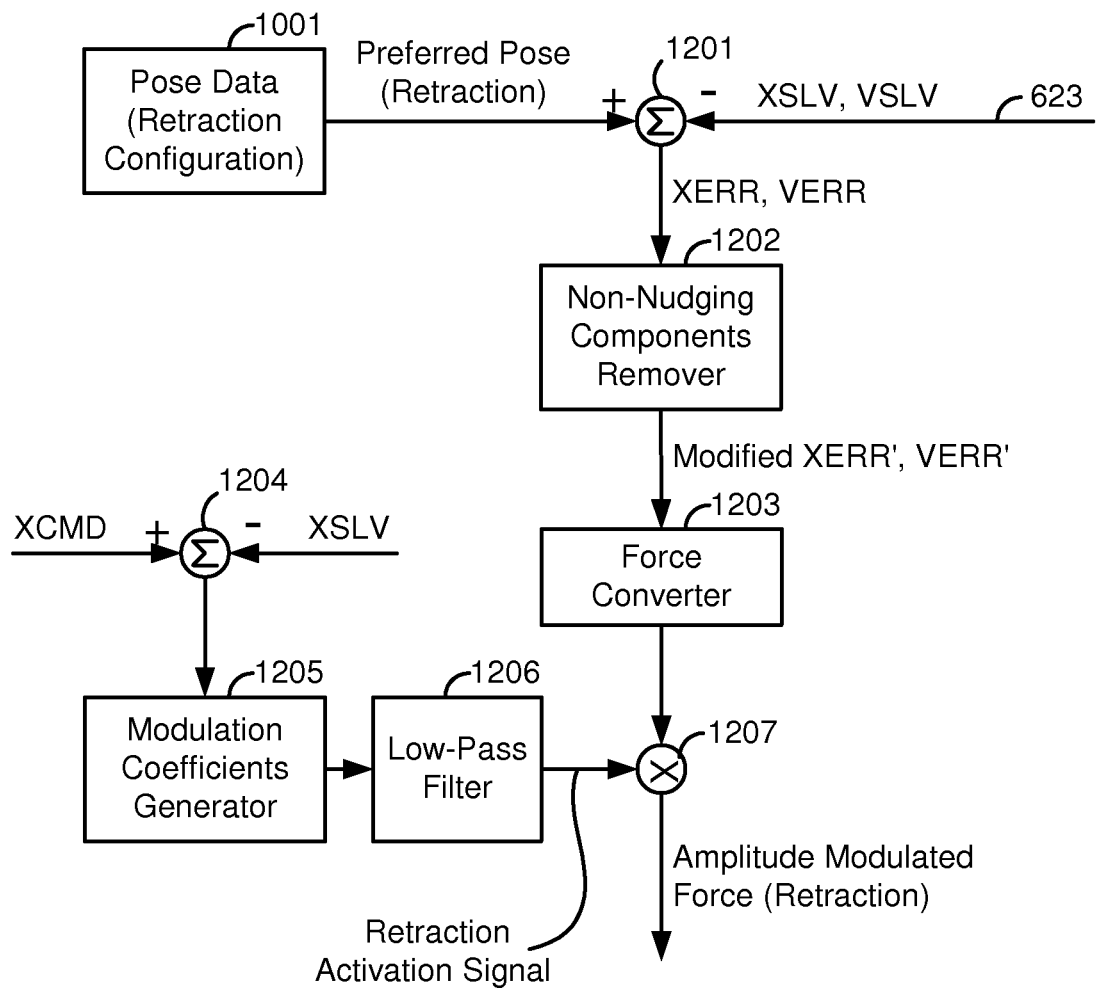
FIG. 12 illustrates a block diagram of the retraction mode nudging block of FIG. 10 as used in a medical robotic system utilizing aspects of the present invention.

FIG. 12 illustrates, as an example, a block diagram of the retraction mode nudging block 1003 which continually processes incoming data. A summing node 1201 computes a difference (XERR, VERR) between the preferred "straightened" pose 1001 (i.e., the retraction configuration for the camera instrument 211) and the modified commanded pose (XSLV, VSLV) 623 which is generated by the virtual barrier logic 901 of the simulated instrument block 608 of the instrument controller 213. As used herein, the term "pose" means both position and orientation of the instrument as well as their positional and rotational velocities, so that the commanded pose may include both positional (XCMD) and velocity (VCMD) components, the modified commanded pose may include both positional (XSLV) and velocity (VSLV) components, the preferred pose may include both positional (XPP) and velocity (VPP) components, and the computed difference between the preferred pose and the modified commanded pose may include both positional (XERR) and velocity (VERR) components. In the computation performed in summing node 1201, however, the velocity (VPP) components of the preferred pose (VPP) are all presumed to be zero.

Figure 15:
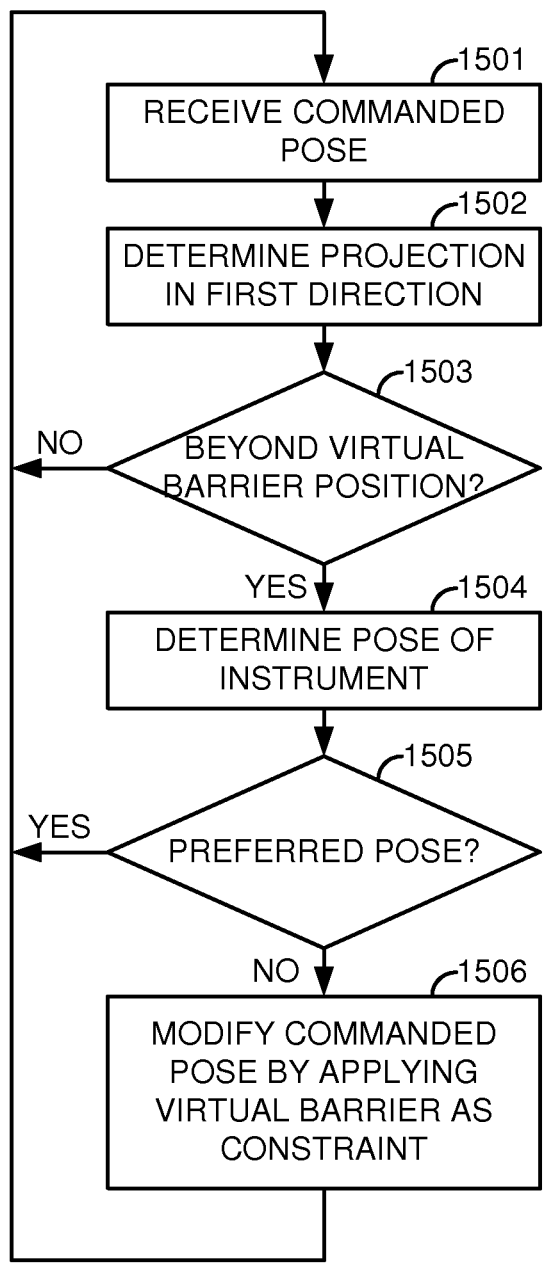
FIG. 15 illustrates a flow diagram of a method for modifying a commanded pose of an articulated instrument by applying a virtual barrier as a constraint as usable in a method for urging operator manipulation of an input device to command the articulated instrument to a preferred pose utilizing aspects of the present invention.

To explain how the modified commanded pose (XSLV, VSLV) is generated, an example of the virtual barrier logic 901 is described in reference to FIG. 15. In block 1501, the logic 901 receives the commanded pose (XCMD) 621 from the scale and offset block 621 and in block 1502, it determines the projection of the commanded pose 621 in a first direction, which in the present example is the instrument retraction direction along the longitudinal axis 401 of the first link 322 of the camera instrument 211. In block 1503, a determination is made whether the projection along the first direction would command the camera instrument 211 to move beyond a virtual barrier position. The virtual barrier position in this case is a position along the longitudinal axis 401 which is a threshold distance or safety margin from the distal end of the entry guide 200. As described in US 2011/0040305 A1, the purpose of the safety margin is to prevent damage from occurring to either or both the entry guide 200 and the articulated instrument 211 when attempting to force the articulated instrument 211 back into the entry guide 200 while it is in a configuration in which it physically will not fit at the time. If the determination in block 1503 is NO, then the virtual barrier logic 901 jumps back to block 1501 to process data for a next process cycle. On the other hand, if the determination in block 1503 is YES, then in block 1504, the current pose of the camera instrument 211 is determined sensing its joint positions and applying forward kinematics to determine their corresponding Cartesian pose. In block 1505, a determination is then made whether the current pose of the camera instrument 211 is the preferred pose (i.e., "straightened" pose in this case). If the determination in block 1505 is YES, then the virtual barrier logic 901 doesn't modify the commanded pose (XCMD) and jumps back to block 1501 to process data for a next process cycle. On the other hand, if the determination n block 1505 is NO, then commanded pose (XCMD) is modified by applying the virtual barrier as constraint so that the camera instrument 211 is prevented from moving further in the first direction. The method then loops back to block 1501 to process data for the next process cycle. Thus, the camera instrument 211 is prevented in this way from moving beyond the virtual barrier position until the current pose is the preferred retraction pose of the camera instrument 211.

Referring back to FIG. 12, in block 1202, non-nudging components of the calculated difference (XERR, VERR) are removed. In particular, translational components along the first direction and the roll rotational component about the tip 310 are removed since neither of these components affects the preferred pose (i.e., regardless of their values, the camera instrument may be placed in a "straightened" pose as shown in FIG. 8). In block 1203, the modified difference (XERR', VERR') generated in block 1202 is converted to generate a force command that would result in one or more forces being applied to the input device 108 so that the Surgeon is urged to command the camera instrument 211 to the preferred pose. Preferably such force command is a visco-elastic six degree-of-freedom force that would be applied to corresponding degrees-of-freedom of the input device 108.

Figure 14:
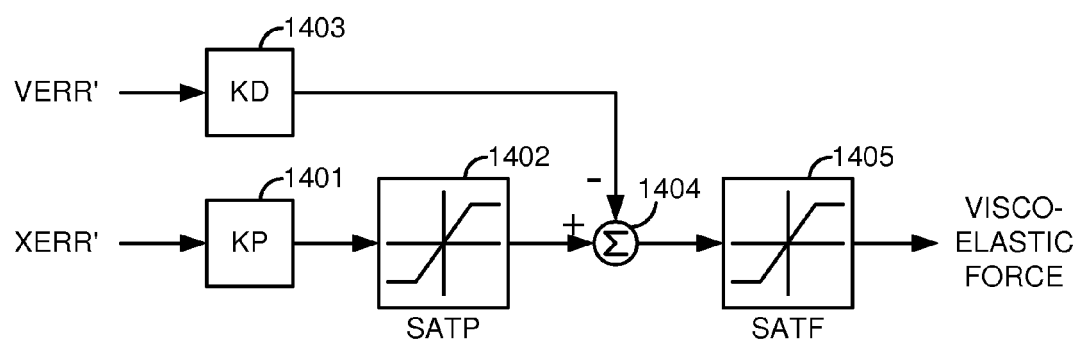
FIG. 14 illustrates a block diagram of the force converter block of FIGS. 12 and 13 as used in a medical robotic system utilizing aspects of the present invention.

An example of the force converter block 1203 is illustrated in FIG. 14 by a block diagram of a Proportional-Derivative (PD) open loop system. In this PD system, the modified position difference (XERR') is multiplied by a position gain (KP) 1401 and limited by limiter 1402 to a first saturation value (SATP) to generate a first force command contribution. At the same time, the modified velocity difference (VERR') is multiplied by a derivative gain (KD) 1403 to generate a second force command contribution. A summing node 1404 calculates a difference between second and first force command contributions and a limiter 1405 limits to the difference to a second saturation value (SATF). The thus limited difference between the second and first force command contributions results in a visco-elastic six degree-of-freedom Cartesian force for nudging the Surgeon to move the input device 108 so as to command the preferred pose. Values for the first and second saturation values are selected so as to ensure that commanded motor torques on the motors of the input device 108 do not exceed their rated maximum values.

Figure 11:
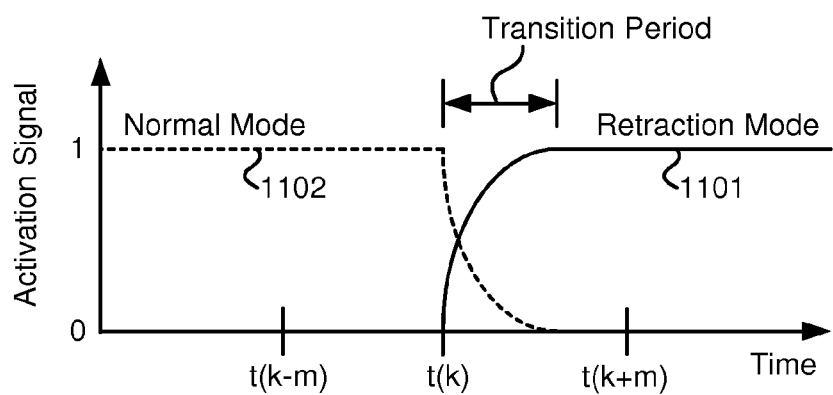
FIG. 11 illustrates activation signals for normal mode operation and retraction mode as a function of time as used in a medical robotic system utilizing aspects of the present invention.

Referring back to FIG. 12, modulator 1207 amplitude modulates the visco-elastic six degree-of-freedom Cartesian force generated by the force converter block 1203 with a retraction activation signal which resembles curve 1101 in FIG. 11. To generate the retraction activation signal, a summing node 1204 calculates a difference between the commanded pose (XCMD) and the modified commanded pose (XSLV), ignoring velocity contributions, modulation coefficients generator 1205 generates a stream of modulation coefficients using the calculated difference, and a low-pass filter 1206 filters the stream of modulation coefficients.

Figure 16:
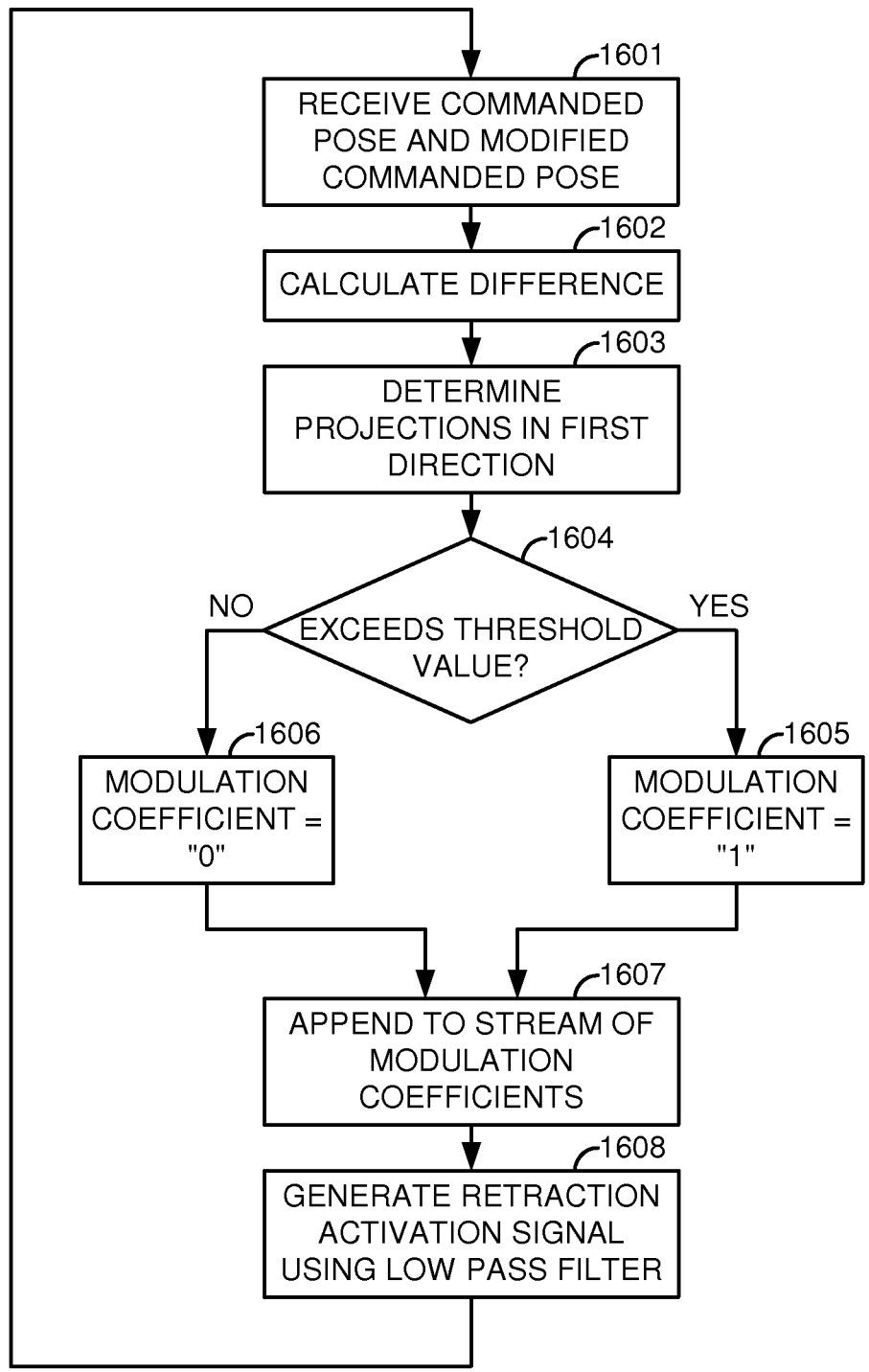
FIG. 16 illustrates a flow diagram of a method for generating a retraction mode activation signal usable in a method for urging operator manipulation of an input device to command the articulated instrument to a preferred pose utilizing aspects of the present invention.

An example of the generation of the retraction mode activation signal is provided in a flow diagram illustrated in FIG. 16. Blocks 1601 and 1602 describe actions taken by the summing node 1204. In particular, in block 1601, the commanded pose (XCMD) and modified commanded pose (XSLV) are received, and in block 1602, a difference between the commanded pose (XCMD) and the modified commanded pose (XSLV) is calculated. Blocks 1603 to 1607 next describe actions taken by the modulation coefficients generator 1205. In block 1603, a projection of the calculated difference in a first direction (i.e., the retraction direction along the longitudinal axis 401) is determined and in block 1604, a determination is made whether the projection exceeds a threshold value. The threshold value in this case should be large enough to ensure that the Surgeon really intends to retract the camera instrument 211 and that it is not an inadvertent action such as may result from hand tremor. If the determination in block 1604 is YES, then in block 1605, the current modulation coefficient is set to an integer value "1". On the other hand, if the determination in block 1604 is NO, then in block 1606, the current modulation coefficient is set to an integer value of "0". In block 1607, the current modulation coefficient is then appended to a stream of modulation coefficients generated in prior process periods. Block 1608 describes action taken by the low-pass filter 1206. In particular, in block 1608, the retraction activation signal is generated by passing the stream of modulation coefficients through the low-pass filter 1206 and the process then jumps back to block 1601 to process data for the next process cycle.

Figure 13:
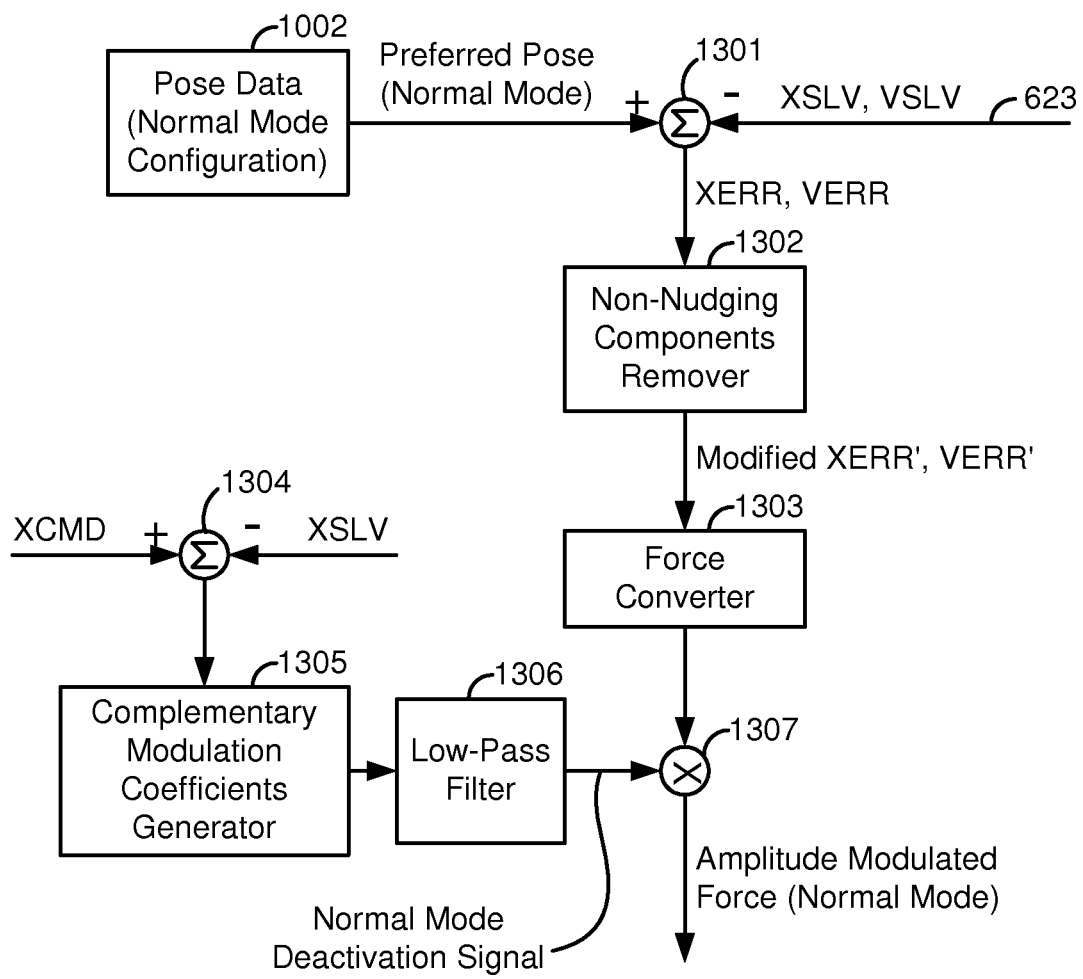
FIG. 13 illustrates a block diagram of the normal mode nudging block of FIG. 10 as used in a medical robotic system utilizing aspects of the present invention.

FIG. 13 illustrates, as an example, a block diagram of the normal mode nudging block 1004 which also continually processes incoming data. A summing node 1301 computes a difference (XERR, VERR) between the preferred "cobra" pose 1002 (i.e., the normal mode configuration for the camera instrument 211) and the modified commanded pose (XSLV, VSLV) 623 which is generated by the virtual barrier logic 901 of the simulated instrument block 608 of the instrument controller 213.

In block 1302, non-nudging components of the calculated difference (XERR, VERR) are removed. In particular, translational components along the first direction and the roll rotational component about the tip 311 are removed since neither of these components affects the preferred pose (i.e., regardless of their values, the camera instrument may be placed in a "cobra" pose as shown in FIG. 7). In block 1303, the modified difference (XERR', VERR') generated in block 1302 is converted to generate a force command that would result in one or more forces being applied to the input device 108 so that the Surgeon is urged to command the camera instrument 211 to the preferred pose. Preferably such force command is a visco-elastic six degree-of-freedom force that would be applied to corresponding degrees-of-freedom of the input device 108, whose generation is similar to that previously described in reference to FIG. 14.

Modulator 1307 then amplitude modulates the visco-elastic six degree-of-freedom Cartesian force generated by the force converter block 1303 with a normal mode deactivation signal which resembles curve 1102 in FIG. 11. To generate the normal mode deactivation signal, a summing node 1304 calculates a difference between the commanded pose (XCMD) and the modified commanded pose (XSLV), ignoring velocity contributions, modulation coefficients generator 1305 generates a stream of modulation coefficients using the calculated difference, and a low-pass filter 1306 filters the stream of modulation coefficients.

Figure 17:
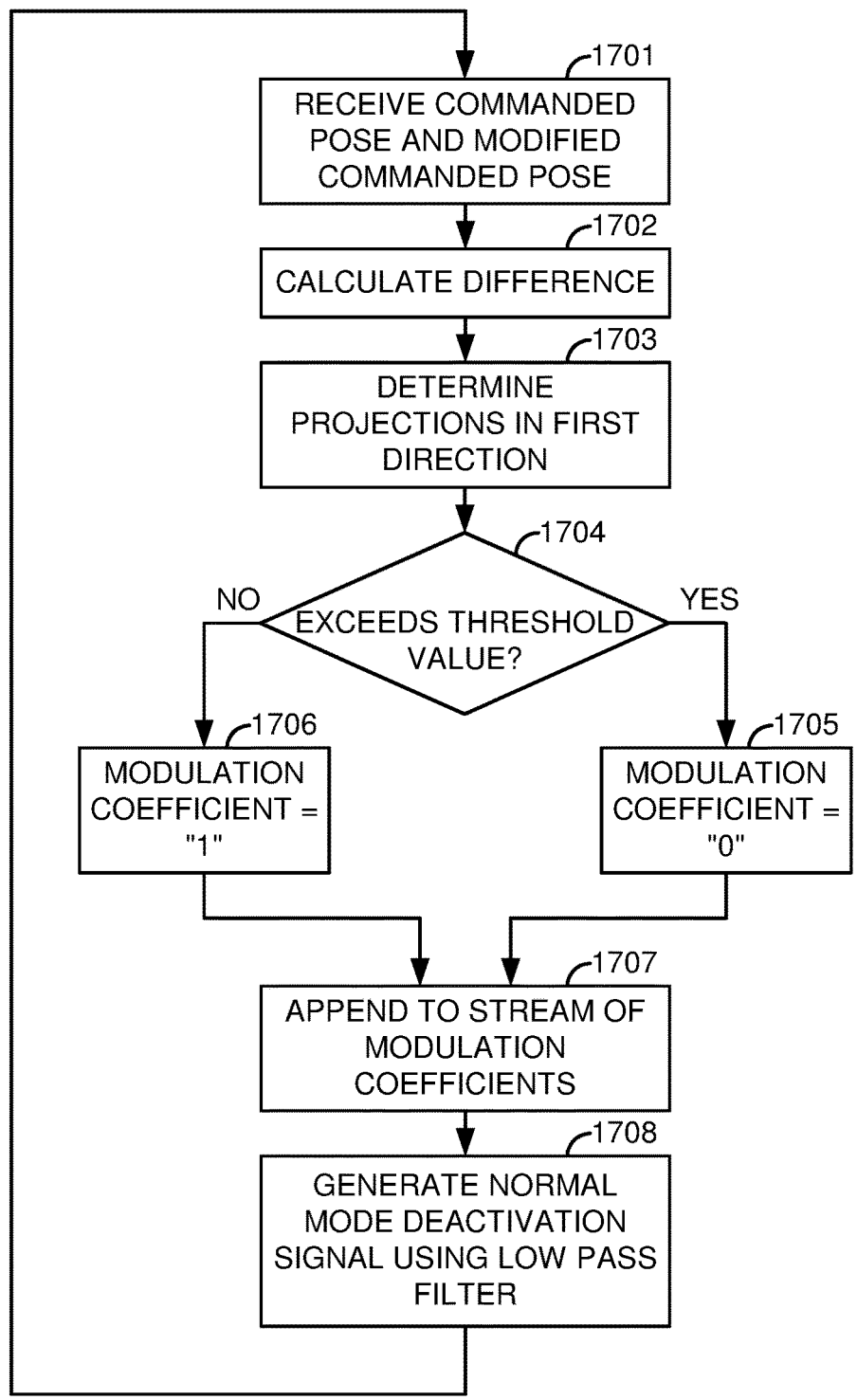
FIG. 17 illustrates a flow diagram of a method for generating a normal mode deactivation signal usable in a method for urging operator manipulation of an input device to command the articulated instrument to a preferred pose utilizing aspects of the present invention.

An example of the generation of the normal mode deactivation signal is provided in a flow diagram illustrated in FIG. 17. Blocks 1701 and 1702 describe actions taken by the summing node 1304. In particular, in block 1701, the commanded pose (XCMD) and modified commanded pose (XSLV) are received, and in block 1702, a difference between the commanded pose (XCMD) and the modified commanded pose (XSLV) is calculated. Blocks 1703 to 1707 next describe actions taken by the modulation coefficients generator 1305. In block 1703, a projection of the calculated difference in a first direction (i.e., the retraction direction along the longitudinal axis 401) is determined and in block 1704, a determination is made whether the projection exceeds a threshold value. The threshold value in this case should be large enough to ensure that the Surgeon really intends to retract the camera instrument 211 and that it is not inadvertent action such as may result from hand tremor. If the determination in block 1704 is YES, then in block 1705, the current modulation coefficient is set to an integer value "0". On the other hand, if the determination in block 1704 is NO, then in block 1706, the current modulation coefficient is set to an integer value of "1". Note that the modulation coefficient value assignments are opposite to those used in the generation of the retraction activation signal, which results in one of the retraction and normal mode activation signals phasing in while the other is phasing out. In block 1707, the current modulation coefficient is then appended to a stream of modulation coefficients generated in prior process periods. Block 1708 finally describes action taken by the low-pass filter 1306. In particular, in block 1708, the normal mode deactivation signal is generated by passing stream of modulation coefficients through the low-pass filter 1306. The process then jumps back to block 1701 to process data for the next process cycle.

The time constants for the low-pass filter 1206 in the retraction mode nudging block 1003 and the low-pass filter 1306 in the normal mode nudging block 1004 are preferably the same so that the phasing in and phasing out match during the transition period such as shown in FIG. 11, where time "t(k)" represents the time that the threshold value determinations in blocks 1804 and 1704 first result in a YES determination, time "t(k−m)" represents a time prior to "t(k)" when the threshold value determinations in blocks 1804 and 1704 resulted in a NO determination, and time "t(k+m)" represents a time after "t(k)" when the threshold value determinations in blocks 1804 and 1704 still result in a YES determination.

Figure 18:
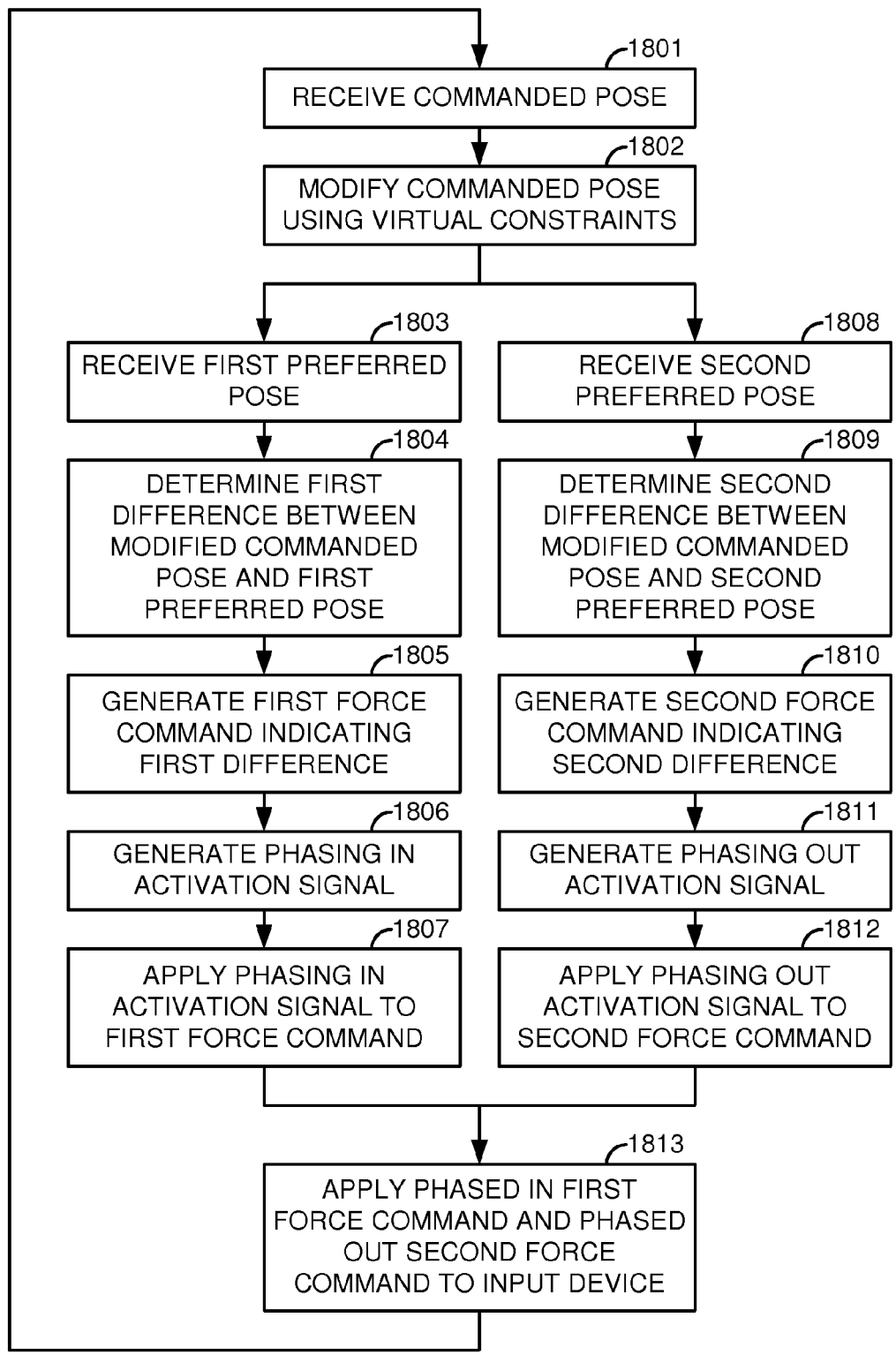
FIG. 18 illustrates a flow diagram of a first embodiment of a method for urging operator manipulation of an input device to command an articulated instrument to a preferred pose utilizing aspects of the present invention.

FIG. 18 illustrates a flow diagram summarizing the first embodiment of the invention as described in detail above. In block 1801, a commanded pose (XCMD) is received from an input device associated at the time with the articulated instrument whose pose is being commanded. In block 1802, the commanded pose is modified using virtual constraints (such as described in reference to FIG. 15). In blocks 1803-1807, a first force command is generated which is to be phased in to nudge the operator of the input device to command a first (new) preferred pose (such as described in reference to FIG. 12) while concurrently in blocks 1808-1812, a second force command is generated which is to be phased out to nudge the operator of the input device to command a second (incumbent) preferred pose (such as described in reference to FIG. 13). In block 1813, the first and second force commands are applied to the input device so that initially the operator of the input device is urged to command the second preferred pose then subsequently after a phasing in and phasing out transition period the operator is urged to command the first preferred pose.

Figure 19:
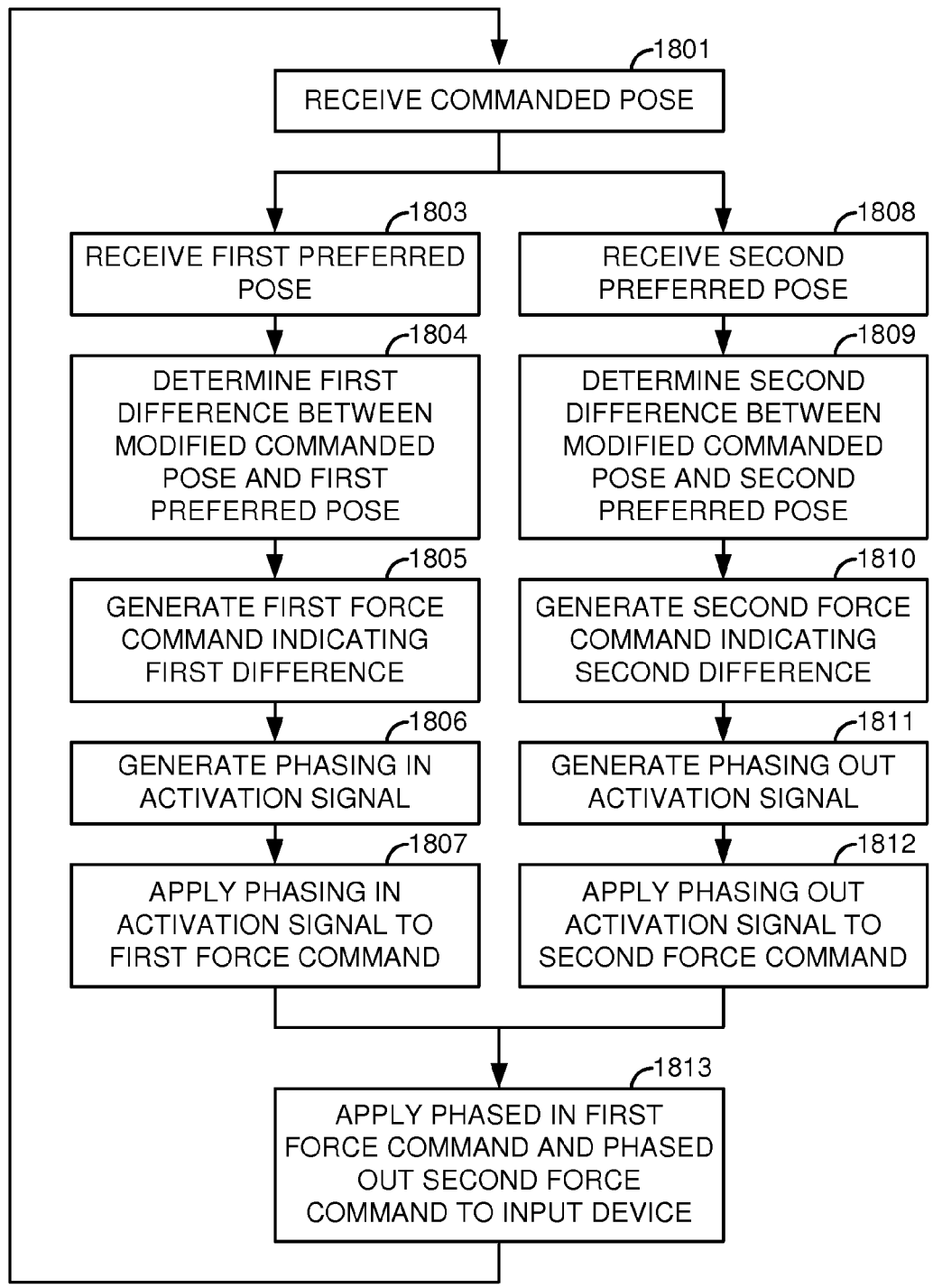
FIG. 19 illustrates a flow diagram of a second embodiment of a method for urging operator manipulation of an input device to command an articulated instrument to a preferred pose utilizing aspects of the present invention.
Figure 20:
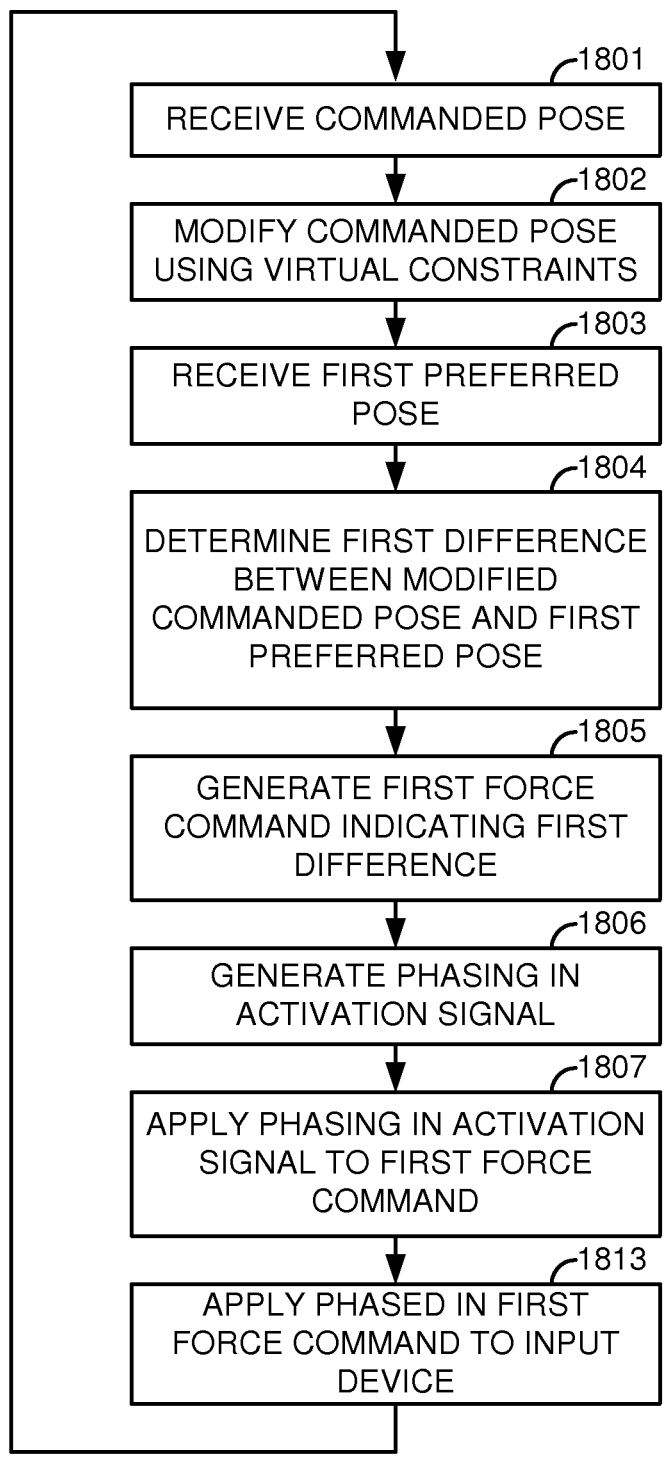
FIG. 20 illustrates a flow diagram of a third embodiment of a method for urging operator manipulation of an input device to command an articulated instrument to a preferred pose utilizing aspects of the present invention.
Figure 21:
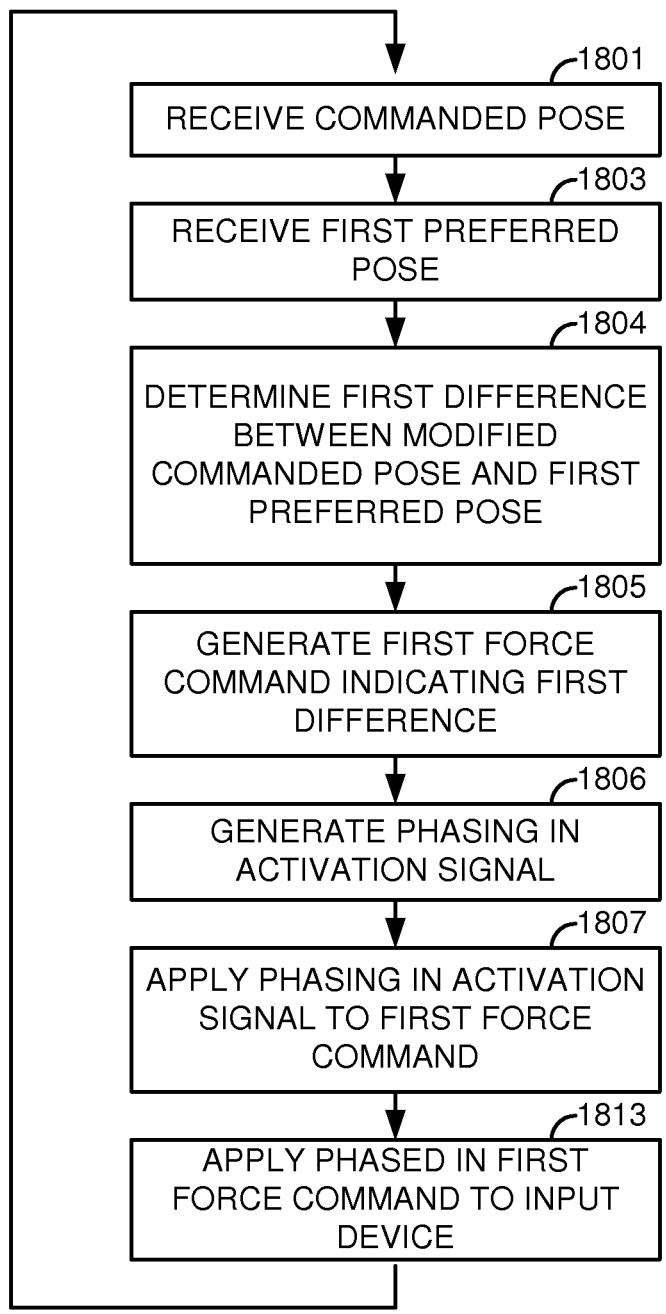
FIG. 21 illustrates a flow diagram of a fourth embodiment of a method for urging operator manipulation of an input device to command an articulated instrument to a preferred pose utilizing aspects of the present invention.

FIGS. 19-21 illustrate additional embodiments of the invention which include various combinations of some, but not all of the blocks described in reference to FIG. 18. In particular, FIG. 19 illustrates a second embodiment that is a modification to the first embodiment, wherein the commanded pose is not modified using virtual constraints by deleting block 1802, but performing all other blocks of the first embodiment. FIG. 20 illustrates a third embodiment that is a modification to the first embodiment, wherein a second (incumbent) preferred pose is not active by deleting blocks 808-812, but performing all other blocks of the first embodiment with block 813 modified since there is no second force command to be phased out. FIG. 21 illustrates a fourth embodiment that is a modification to the third embodiment, wherein the commanded pose is not modified using virtual constraints by deleting block 1802, but performing all other blocks of the third embodiment.

Figure 22:
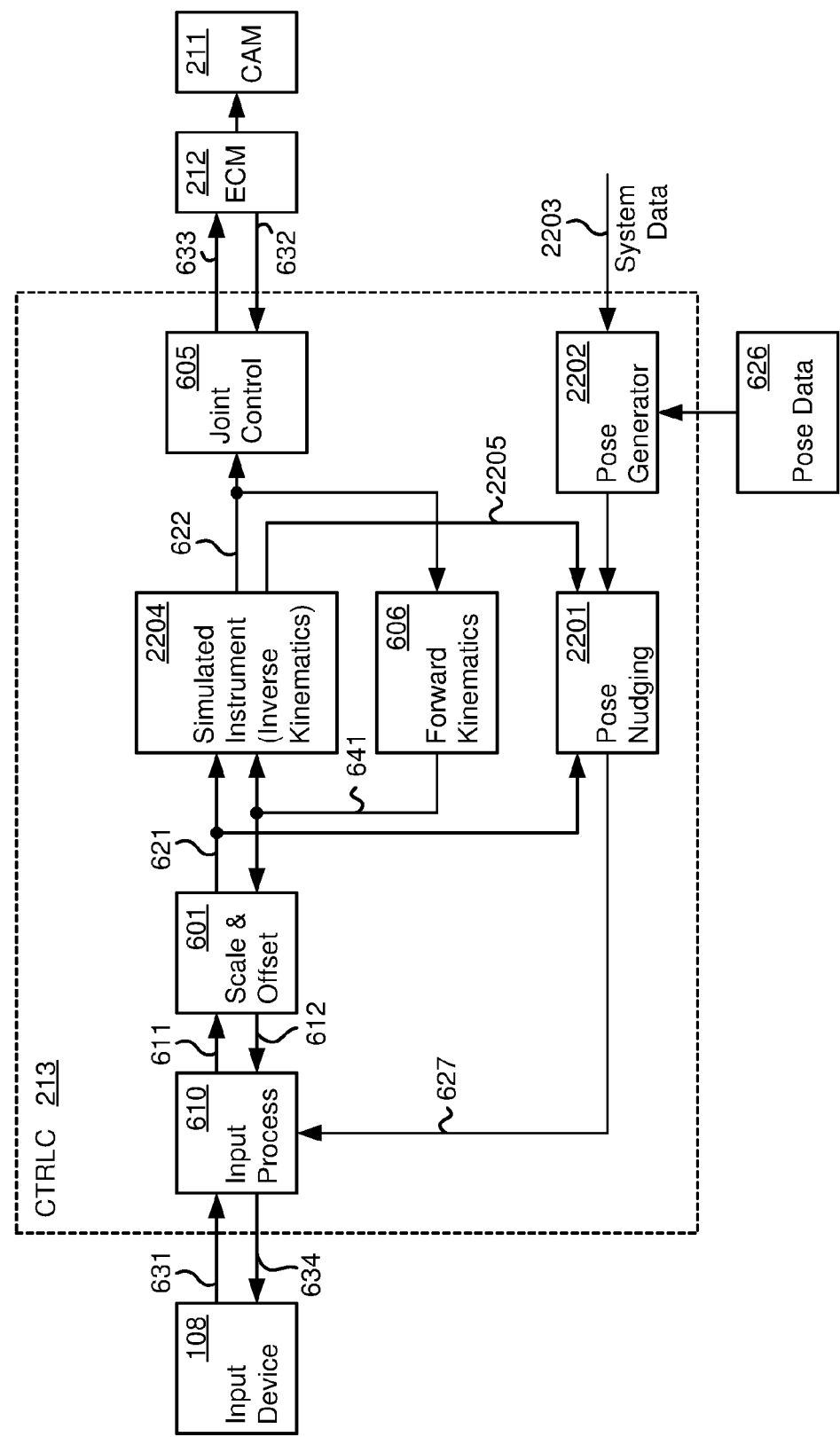
FIG. 22 illustrates a block diagram of an alternative instrument controller for operator commanded movement of an articulated instrument in a medical robotic system utilizing aspects of the present invention.
Figure 23:
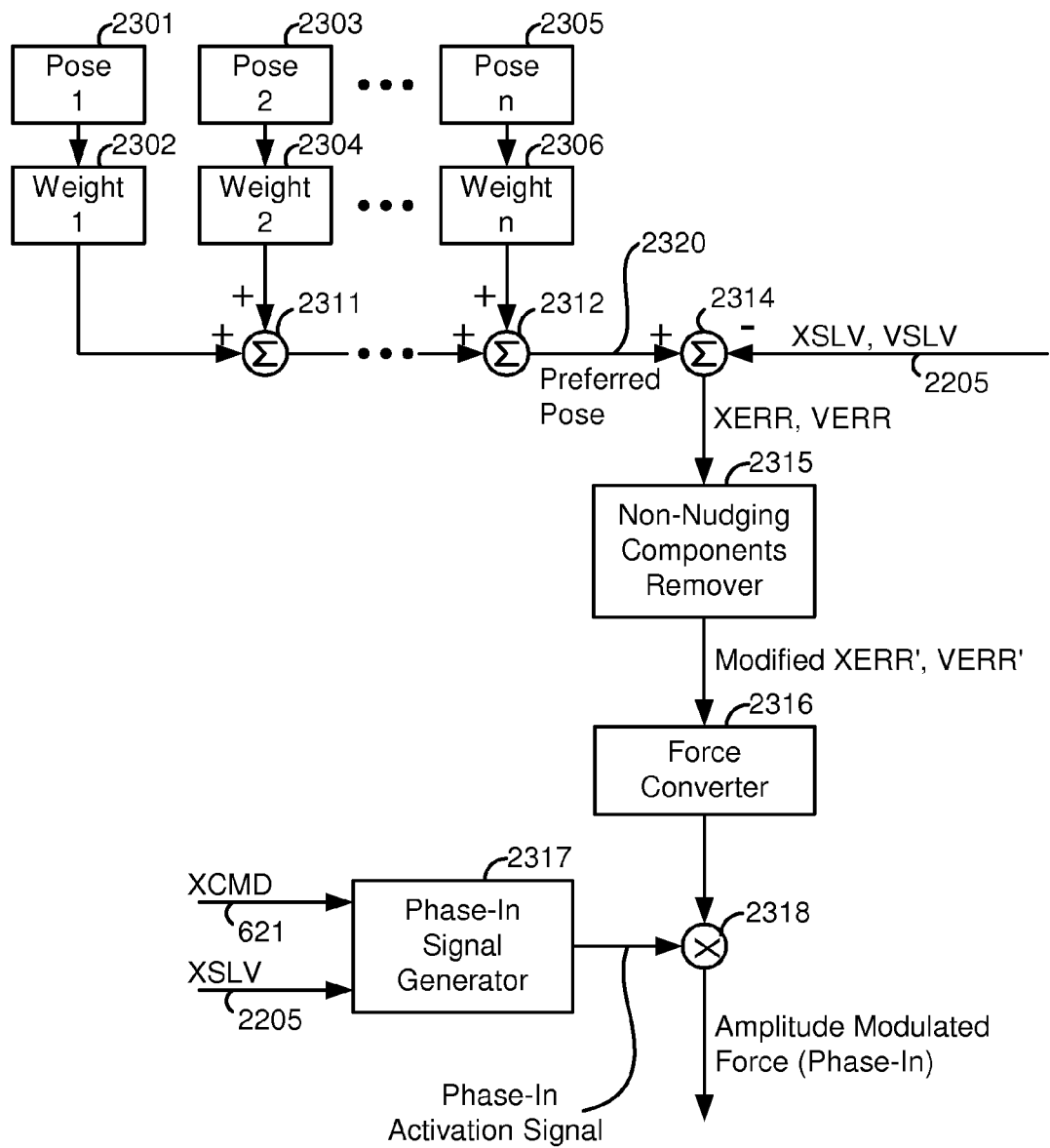
FIG. 23 illustrates a block diagram of a "phase-in" nudging block providing a first nudging force command which is to be phased-in as a force to be applied against an input control device, as used in a medical robotic system utilizing aspects of the present invention.
Figure 24:
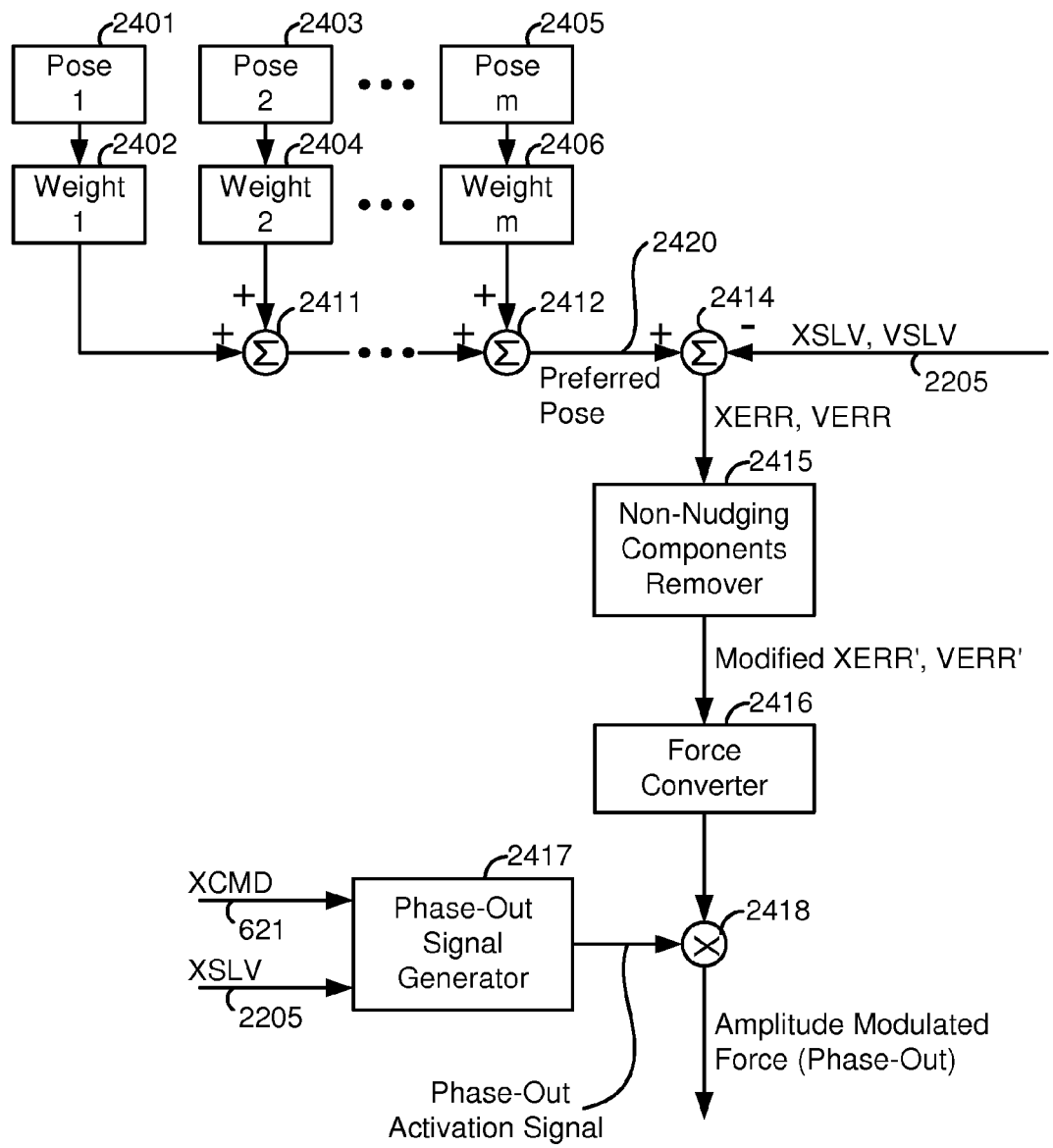
FIG. 24 illustrates a block diagram of a "phase-out" nudging block providing a second nudging force command which is to be phased-out as a force being applied against an input control device, as used in a medical robotic system utilizing aspects of the present invention.

FIGS. 22-24 illustrate still other embodiments of the invention which expand upon some of the previously disclosed embodiments. In particular, whereas prior embodiments disclose a single preferred pose being active at a time (outside a transition period), the embodiments shown in FIGS. 22-24 contemplate the possibility of multiple preferred poses being active at a time with the active preferred poses being weighted so that one or some may be more dominant than others. Further, the weightings provide an additional mechanism through which preferred poses may be transitioned in and out by making their respective weightings dynamically alterable (e.g., progressively changing from a weighting of "0" to a weighting of "1" to phase the corresponding preferred pose in and conversely, progressively changing from a weighting of "1" to a weighting of "0" to phase the corresponding preferred pose out). Also, whereas prior embodiments disclose fixed preferred poses for different operating modes, the embodiments shown in FIGS. 22-24 contemplate the possibility of dynamically changing preferred poses based upon system data such as the current or commanded poses of other articulated instruments. For example, the preferred pose for the camera instrument 211 may dynamically change as the poses of the end effectors 331, 341 of the tool instruments 231, 241 change so that the end effectors 331, 341 remain well positioned in a field of view of the camera instrument 211. As another example, the preferred poses of each of the articulated instruments 211, 231, 241 may dynamically change to avoid collisions with others of the articulated instruments 211, 231, 241 during the performance of a medical procedure using the articulated instruments 211, 231, 241.

FIG. 22 illustrates, for example, a block diagram of an alternative instrument controller for operator commanded movement of an articulated instrument. Although the example is for the camera controller 213, it is to be appreciated that the same general structure may be used for other device controllers 203, 233, 243 in the medical robotic system 100. The functions of blocks 610, 601, 605, 606 are the same as previously described in reference to FIG. 6. The function of the simulated instrument block 2204 is generally the same as block 604 of FIG. 6 with regards to inverse kinematics and limiting, but may differ in regards to virtual constraints imposed on the commanded pose 621 to generate a modified commanded pose 2205, because of different operating modes and/or preferred poses. Likewise, the function of pose nudging block 2201 is generally the same as block 625 with regards to summing together two pose nudging contributions wherein a first (new) preferred pose is to be phased in while a second (incumbent) preferred pose is to be phased out according to respective activation signals.

A pose generator block 2202 is included in the controller 213 to dynamically generate one or more preferred poses that are provided to the pose nudging block 2201, as well as pass through static preferred poses when appropriate. In particular, although a static preferred pose provided by the pose data block 626 may be normally passed through, the preferred pose for the articulated camera instrument 211 may dynamically be changed from the static preferred pose as conditions, such as the poses of other tool instruments 231, 241 around it, change. As one example, the preferred pose for the camera instrument 211 may dynamically change during normal operating mode to avoid collisions with the tool instruments 231, 241, which are being used and therefore, moving at the time to perform a medical procedure on a patient anatomy. To dynamically generate one or more preferred poses to be phased in (such as preferred poses 2301, 2303, 2305 of FIG. 23) and one or more preferred poses to be phased out (such as preferred poses 2401, 2403, 2405), the pose generator block 2202 may use a different function of one or more states of the system for each of the preferred poses to be dynamically changed. The system state information in this case is provided by system data 2203. As one example, the system data 2203 may comprise the commanded poses of other instruments 231, 241 in the system 100. As another example, the system data 2203 may comprise the actual poses of the other instruments 231, 241 as determined by applying forward kinematics to their sensed joint positions.

The pose nudging block 2201 includes "phase-in" and "phase-out" nudging blocks which respectively generate nudging forces that are to be phased-in and phased-out on the input device 108 in a similar manner as previously described with respect to the retraction mode and normal mode nudging blocks, 1003 and 1004, of FIG. 10.

FIG. 23 illustrates, as an example, a block diagram of the "phase-in" nudging block. A preferred pose 2320 is generated by a weighted average of a plurality of preferred poses (e.g., preferred poses 2301, 2303, 2305) so that each of the preferred poses is multiplied by a corresponding weight (e.g., weights 2302, 2304, 2306) with the sum of the weights equal to "1". The weights may be fixed values or preferably dynamic values so one or more of the preferred poses may be dominant at different times, in different operating modes or under different system conditions. A difference between the preferred pose 2320 and the modified commanded pose 2205 is computed by summing node 2314. Non-nudging components of the difference are removed in block 2315 and the result provided to force converter block 2316 which generates a force command such as described in reference to block 1203 of FIG. 12. A phase-in activation signal is generated by phase-in signal generator block 2317 so as to resemble the retraction mode activation signal 1101 in FIG. 1I. An amplitude modulated force command, which is to be phased-in on the input device 108, is then generated by amplitude modulator 2318 by amplitude modulating the force command generated by the force converter block 2316 with the phase-in activation signal.

Using a similar construction, FIG. 24 illustrates, as an example, a block diagram of the "phase-out" nudging block. A preferred pose 2420 in this case is generated by a weighted average of a plurality of preferred poses (e.g., preferred poses 2401, 2403, 2405) so that each of the preferred poses is multiplied by a corresponding weight (e.g., weights 2402, 2404, 2406) with the sum of the weights equal to "1". The weights may be fixed values or preferably dynamic values so one or more of the preferred poses may be dominant at different times, in different operating modes or under different system conditions. A difference between the preferred pose 2420 and the modified commanded pose 2205 is computed by summing node 2414. Non-nudging components of the difference are removed in block 2415 and the result provided to force converter block 2416 which generates a force command such as described in reference to block

1203 of FIG. 12. A phase-out activation signal is generated by phase-out signal generator block 2417 so as to resemble the normal mode activation signal 1102 in FIG. 11. An amplitude modulated force command, which is provided to and is to be phased-out on the input device 108, is then generated by amplitude modulator 2418 by amplitude modulating the force command generated by the force converter block 2416 with the phase-out activation signal.

In addition to the embodiments described herein, it is to be appreciated that other embodiments may be constructed, and are fully contemplated to be within the scope of the present invention, through different combinations of their various teachings. In particular, although the various aspects of the present invention have been described with respect to preferred and alternative embodiments, it will be understood that the invention is entitled to full protection within the full scope of the appended claims.

What is claimed is:

1. A method for urging operator manipulation of an input device to command an articulated instrument to a preferred pose, the method comprising:
   generating a commanded pose of the articulated instrument in response to operator manipulation of the input device;
   modifying the commanded pose by applying a virtual barrier as a constraint to prevent the articulated instrument from being commanded to move beyond the virtual barrier until at least a portion of the articulated instrument which is closest to, but has not yet encountered the virtual barrier conforms with a first preferred pose;
   generating a stream of modulation coefficients indicative of a difference between the commanded pose and the modified commanded pose;
   generating a first activation signal by processing the stream of modulation coefficients;
   generating first force commands for a first plurality of degrees of freedom of the input device so as to be indicative of a difference between the first preferred pose and the commanded pose; and
   applying the first force commands to the first plurality of degrees of freedom of the input device by phasing in their application according to the first activation signal.

2. The method of claim 1, wherein generating the first activation signal comprises filtering the stream of modulation coefficients by using a low pass filter.

3. The method of claim 1,
   wherein the constraint prevents the articulated instrument from being commanded to move beyond the virtual barrier in a first direction, and
   wherein generating the stream of modulation coefficients comprises:
      determining a difference between the commanded pose and the modified commanded pose,
      projecting the difference along the first direction, and
      binary coding the projected difference by setting a current modulation coefficient to a first value when the projected difference is greater than a threshold value and setting the current modulation coefficient to a second value when the projected difference is less than or equal to the threshold value.

4. The method of claim 1,
   wherein the constraint prevents the articulated instrument from being commanded to move beyond the virtual barrier in a first direction, and
   wherein generating the first force commands comprises:
      comparing the first preferred pose to the modified commanded pose to generate Cartesian position and velocity errors;
      modifying the Cartesian position and velocity errors by removing components along the first direction and about an axis of a pivotable tip of the articulated instrument; and
      generating a visco-elastic six degree-of-freedom force command using the modified Cartesian position and velocity errors.

5. The method of claim 4,
   wherein generating of the visco-elastic six degree-of-freedom force command comprises:
      amplifying the modified Cartesian position error by a position gain to generate a first result and limiting the first result to a position saturation limit to generate a second result;
      amplifying the modified Cartesian velocity error by a velocity gain to generate a third result;
      generating an interim visco-elastic six-degree-of-freedom force command by subtracting the third result from the second result; and
      generating the visco-elastic six degree-of-freedom force command by limiting the interim visco-elastic six-degree-of-freedom force command to a force saturation limit.

6. The method of claim 4, wherein applying the first force commands to the first plurality of degrees of freedom of the input device by phasing in their application according to the first activation signal comprises:
   amplitude modulating the visco-elastic six degree-of-freedom force command with the first activation signal.

7. The method of claim 1, further comprising:
   generating second force commands for a second plurality of degrees of freedom of the input device so as to be indicative of a difference between a second preferred pose and the commanded pose;
   applying the second force commands to the second plurality of degrees of freedom of the input device prior to phasing in the application of the first force commands according to the first activation signal; and
   phasing out application of the second force commands according to a second activation signal.

8. The method of claim 7, wherein the constraint prevents the articulated instrument from being commanded to move beyond the virtual barrier in a first direction, the method further comprising:
   generating a second stream of modulation coefficients by determining a difference between the commanded pose and modified commanded pose, projecting the difference along the first direction, and binary coding the projected difference by setting a current modulation coefficient to a second value when the projected difference is greater than a threshold value and setting the current modulation coefficient to a first value when the projected difference is less than or equal to the threshold value; and
   generating the second activation signal by filtering the second stream of modulation coefficients.

9. The method of claim 7, wherein the first and second activation signals are complementary signals so that the first activation signal is phased in as the second activation signal is phased out.

10. A robotic system comprising:
    an input device;
    an articulated instrument; and
    a processor programmed to:

generate a commanded pose of the articulated instrument in response to operator manipulation of the input device, modify the commanded pose by applying a virtual barrier as a constraint to prevent the articulated instrument from being commanded to move beyond the virtual barrier until at least a portion of the articulated instrument which is closest to, but has not yet encountered the virtual barrier conforms with a first preferred pose, generate a stream of modulation coefficients indicative of a difference between the commanded pose and the modified commanded pose, generate a first activation signal by processing the stream of modulation coefficients, generate first force commands for a plurality of degrees of freedom of the input device so as to be indicative of a difference between the first preferred pose and the commanded pose, and command application of the first force commands on the plurality of degrees of freedom of the input device so as to phase in their application according to the first activation signal.

11. The system of claim 10, wherein the processor is programmed to generate the first activation signal by filtering the stream of modulation coefficients by using a low pass filter.

12. The system of claim 10,
wherein the constraint prevents the articulated instrument from being commanded to move beyond the virtual barrier in a first direction, and
wherein the processor is programmed to generate the stream of modulation coefficients by:
determining a difference between the commanded pose and the modified commanded pose,
projecting the difference along the first direction, and
binary coding the projected difference by setting a current modulation coefficient to a first value when the projected difference is greater than a threshold value and setting the current modulation coefficient to a second value when the projected difference is less than or equal to the threshold value.

13. The system of claim 10,
wherein the constraint prevents the articulated instrument from being commanded to move beyond the virtual barrier in a first direction, and
wherein the processor is programmed to generate the first force commands by:
comparing the first preferred pose to the modified commanded pose to generate Cartesian position and velocity errors,
modifying the Cartesian position and velocity errors by removing components along the first direction and about an axis of a pivotable tip of the articulated instrument, and
generating a visco-elastic six degree-of-freedom force command using the modified Cartesian position and velocity errors.

14. The system of claim 13, wherein the processor is programmed to generate the visco-elastic six degree-of-freedom force command by:
amplifying the modified Cartesian position error by a position gain to generate a first result and limiting the first result to a position saturation limit to generate a second result,
amplifying the modified Cartesian velocity error by a velocity gain to generate a third result,
generating an interim visco-elastic six-degree-of-freedom force command by subtracting the third result from the second result, and
generating the visco-elastic six degree-of-freedom force command by limiting the interim visco-elastic six-degree-of-freedom force command to a force saturation limit.

15. The system of claim 13, wherein the processor is programmed to command application of the first force commands on the plurality of degrees of freedom of the input device so as to phase in their application according to the first activation signal by generating an amplitude modulated force by amplitude modulating the visco-elastic six degree of freedom force with the first activation signal and commanding application of the amplitude modulated force on input device.

16. The system of claim 10, wherein the processor is programmed to generate second force commands for a plurality of degrees of freedom of the input device so as to be indicative of a difference between a second preferred pose and the commanded pose; apply the second force commands to the plurality of degrees of freedom of the input device prior to phasing in the application of the first force commands according to the first activation signal; and phase out application of the second force commands according to a second activation signal.

17. The system of claim 16,
wherein the constraint prevents the articulated instrument from being commanded to move beyond the virtual barrier in a first direction,
wherein the processor is programmed to generate a second stream of modulation coefficients by determining a difference between the commanded pose and the modified commanded pose, projecting the difference along the first direction, and binary coding the projected difference by setting a current modulation coefficient to a second value when the projected difference is greater than a threshold value and setting the current modulation coefficient to a first value when the projected difference is less than or equal to the threshold value, and
wherein the processor is programmed to generate the second activation signal by filtering the second stream of modulation coefficients.

18. The system of claim 17, wherein the first and second activation signals are complementary signals so that the first activation is phased in as the second activation signal is phased out.

19. The system of claim 10,
wherein the processor is programmed to generate the first preferred pose by using a weighted average of a first plurality of preferred poses, and
wherein at least one of the first plurality of preferred poses is a function of at least one state of the system.

20. A non-transient computer readable medium containing program instructions for causing a computer to perform the method of:
generating a commanded pose of an articulated instrument in response to operator manipulation of an input device;
modifying the commanded pose by applying a virtual barrier as a constraint to prevent the articulated instrument from being commanded to move beyond the virtual barrier until at least a portion of the articulated instrument which is closest to, but has not yet encountered the virtual barrier conforms with a first preferred pose;

generating a stream of modulation coefficients indicative of a difference between the commanded pose and the modified commanded pose;
generating a first activation signal by processing the stream of modulation coefficients;
generating first force commands so as to be indicative of a difference between the first preferred pose and the commanded pose; and
applying the first force commands to the input device by phasing in their application according to the first activation signal.

* * * * *